US007063949B2

(12) United States Patent
Granoff et al.

(10) Patent No.: US 7,063,949 B2
(45) Date of Patent: Jun. 20, 2006

(54) **METHODS FOR ISOLATING MOLECULAR MIMETICS OF UNIQUE *NEISSERIA MENINGITIDIS* SEROGROUP B EPITOPES**

(75) Inventors: Dan M. Granoff, Berkeley, CA (US); Gregory R. Moe, Alameda, CA (US)

(73) Assignees: Chiron Corporation, Emeryville, CA (US); Children's Hospital Medical Center of Northern California, Oakland, CA (US)

( * ) Notice: Subject to any disclaimer, the term of this patent is extended or adjusted under 35 U.S.C. 154(b) by 15 days.

(21) Appl. No.: 10/643,465

(22) Filed: Aug. 19, 2003

(65) Prior Publication Data

US 2004/0077840 A1    Apr. 22, 2004

Related U.S. Application Data

(60) Division of application No. 09/910,552, filed on Jul. 23, 2001, now Pat. No. 6,642,354, which is a division of application No. 09/494,822, filed on Jan. 31, 2000, now abandoned, which is a continuation of application No. 08/925,002, filed on Aug. 27, 1997, now Pat. No. 6,048,527.

(60) Provisional application No. 60/025,799, filed on Aug. 27, 1996.

(51) Int. Cl.
*G01N 33/53* (2006.01)
*G01N 33/00* (2006.01)
*C12N 7/01* (2006.01)
*C07K 1/00* (2006.01)

(52) U.S. Cl. ............... 435/7.1; 435/235.1; 435/272; 436/86

(58) Field of Classification Search ............ 435/274, 435/272, 971, 965, 961, 7.1, 235.1, 72; 436/538, 436/86, 824; 530/300, 334, 344
See application file for complete search history.

(56) References Cited

U.S. PATENT DOCUMENTS

| 4,356,170 | A |    | 10/1982 | Jennings et al. | ............ 424/88 |
| 4,727,136 | A |    | 2/1988  | Jennings et al. | ............ 530/395 |
| 4,970,070 | A |    | 11/1990 | Raff             | ............ 424/142.1 |
| 5,576,002 | A |    | 11/1996 | Jennings et al. | ............ 424/197.11 |
| 5,683,699 | A |    | 11/1997 | Jennings        | ............ 424/197.11 |
| 5,811,102 | A |    | 9/1998  | Jennings et al. | ............ 424/197.11 |
| 5,902,586 | A |    | 5/1999  | Jennings et al. | ............ 424/178.1 |
| 5,969,130 | A |    | 10/1999 | Jennings et al. | ............ 536/29.1 |
| 6,030,619 | A |    | 2/2000  | Granoff et al.  | ............ 424/185.1 |
| 6,048,527 | A |    | 4/2000  | Granoff et al.  | ............ 424/150.1 |
| 6,638,513 | B1| *  | 10/2003 | Seid             | ............ 424/197.11 |

FOREIGN PATENT DOCUMENTS

| EP | 0 1 45 359 A2 | 6/1985 |
| EP | 0 504 202 B1  | 9/1992 |
| WO | WO 90/06696   | 6/1990 |
| WO | WO 91/08772   | 6/1991 |
| WO | WO 96/14086   | 5/1996 |
| WO | WO98/08543    | 3/1998 |

OTHER PUBLICATIONS

U.S. Appl. No. 10/121,456, filed Apr. 11, 2002, Granoff et al, Not published.
Ashton et al., *Microb. Patheogeneis* 6:455-458 (1989).
Ashton et al., In: *Neisseria 1990*, Achtman M. (Ed.), Walter De Gruyter & Co. Berlin pp. 187-191 (1991).
Bartoloni et al., *Vaccine* 13(5):463-470 (1995).
Baumann et al., *Biochemistry* 32:4007-4013 (1993).
Bitter-Suermann et al., *Immunol. Res*. pp. 225-237 (1987).
Bowie et al., *Science* 247:1306-1310, 1990.
Brisson et al., Helical Epitope of the Group B Meningococcal α(2-8)-Linked Sialic Acid Polysaccharide, *Biochemistry* 31:4996-5004 (1992).
Burgess et al., *J. Cell Biol*. 111:2129-2138, 1990.
Cross et al., *J. Infect. Dis*. 147(1):68-76 (1983).
Devi et al., *FEMS Immunol. Med. Microbiol*. 14:211-220 (1996).
Devi et al., In:*Neisseria:Proc. Ninth Internet. Pathogenic Neisseria Conference FEMS Immunolog. Med. Microbiol.* Evans et al. (Ed.), S.C.C., England pp. 427-429 (1994).
Dubois et al., A Monoclonal Antibody Against *Meningococcus* Group B Polysaccharides Used to Immunocapture and Quantify Polysialylated NCAM in Tissues and Biological Fluids, *Journal of Immunological Methods* 181:125-135 (1995).
Frasch, Carl E., Meningococcal Vaccines: Past, Present and Future, *Meningococcal Disease* 245-283 (1995).
Frosch et al., *PNAS* 82:1194-1198 (1985).
Fusco et al., Preclinical Evaluation of a Novel Group B Meningococcal Conjugate Vaccine that Elicits Bactericidal Activity in Both Mice and Nonhuman Primates, *The Journal of Infectious Disease* 175:364-372 (1997).
Granoff et al., *J. Immunology* 160:5028-5036 (1998).

(Continued)

Primary Examiner—S. Devi
(74) Attorney, Agent, or Firm—Roberta L. Robins; Nicole M. Fortune; Alisa A. Harbin

(57) ABSTRACT

Novel bactericidal antibodies against *Neisseria meningitidis* serogroup B ("MenB") are disclosed. The antibodies either do not cross-react or minimally cross-react with host tissue polysialic acid and hence pose minimal risk of autoimmune activity. The antibodies are used to identify molecular mimetics of unique epitopes found on MenB or *E. coli* K1. Examples of such peptide mimetics are described that elicit serum antibody capable of activating complement-mediated bacteriolysis of MenB. Vaccine compositions containing such mimetics can be used to prevent MenB or *E. coli* K1 disease without the risk of evoking autoantibody.

4 Claims, 15 Drawing Sheets

OTHER PUBLICATIONS

Figure 2:
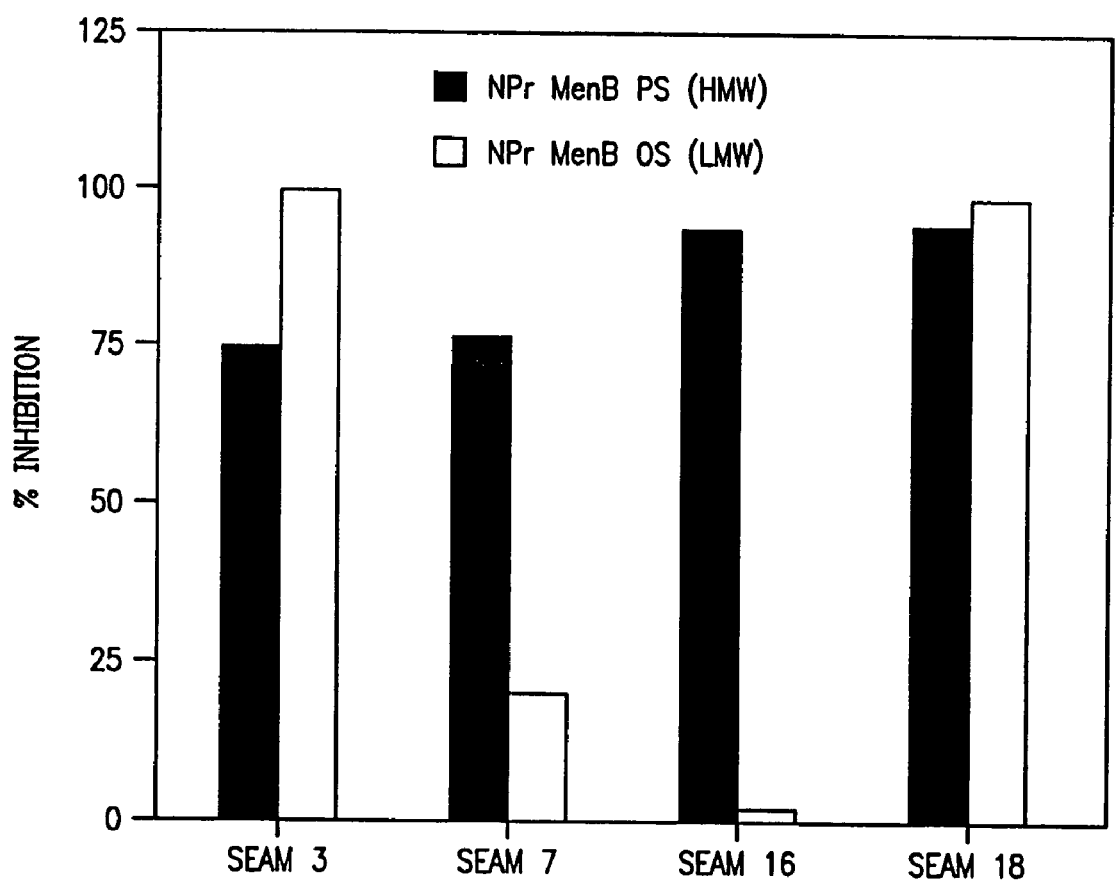

Granoff et al., Antibody Responses to the Capsular Polysaccharide of *Neisseria Menignitidis* Serogroup B in Patients With Meningococcal Disease, *Clinical and Diagnostic Laboratory Immunology* 2(5):574-582 (1995).
Gregson et al., *Biochem. Soc. Transact.* 13:p.462 (1985).
Hayrinen et al., Antibodies to Polysialic Acid and its N-Propyl Derivative: Binding Properties and Interaction with Human Embryonal Brain Glycopeptides, *The Journal Of Infectious Diseases* 171:0001-0010 (1995).
Horwell, David C., The 'Peptoid' Approach to the Design of Non-Peptide, Small Molecule Agonist and Antagonists of Neuropeptides, *TIBTech* 13(4):132-134 (1995).
Hurpin et al., *Hybridoma* 11(6):677-687 (1992).
Husmann et al., *J. Histochem. Cytochem.* 38:209-215 (1990).
Jennings, Harold J., The Capsular Polysaccharide of Group B *Neisseria Meningitidis* as a Vehicle for Vaccine Development, *Microbiol. Immunol.* 10:151-165 (1989).
Jennings et al., Induction of *Meningococcal* Group B Polysaccharide-Specific IgG Antibodies in Mice by Using an N-Propionylated B Polysaccharide-Tetanus Toxoid Conjugate Vaccine, *The J. Of Immunology* 137(5):1708-1713 (1986).
Jennings et al., N-Polysialic Group B Meningococcal Polysaccharide Mimic a Unique Epitope on Group B *Neisseria meningitidis, J. Experimental Medicine* 165:1207-1211 (1987).
Jennings et al., Unique Intermolecular Bactericidal Epitope Involving the Homosialopolysaccharide Capsule on the Cell Surface of Group B *Neisseria meningitidis* and *Escherichia coli* K1, *Journal of Immunology* 142(10):3585-3591 (1989).
Jennings et al., Immunochemistry of Groups A,B, and C Meningococcal Polysaccharide-Tetanus Toxoid Conjugates, *The Journal of Immunology* 127(3):1011-1018 (1981).
Kabat et al., *J. Exp. Med.* 164:642-654 (1986).
Klebert et al., *Biol. Chem. Hoppe Seyler* 374:993-1000 (1993).
Lazar et al., *Mol. Cellular Biol.* 8:1247-1252, 1988.
Leinonen et al., *Infect. Immun.* 38(3):1203-1207 (1982).
Lifely et al., *Immunology* 74:490-496 (1991).
Livingston et al., *J. Biol. Chem.* 263:9443-9448 (1988).
Lommatzsch et al., *J. Bacteriol.* 179:5465-5470 (1997).
Lucas et al., Functional Differences in Idiotypically Defined IgG1 Anti-Polysaccharide Antibodies Elicited by Vaccination with *Haemophilus influenzae* Type B Polysaccharide-Protein Conjugates, *The Journal of Immunology* 154:4195-4202 (1995).
Mandrell et al., Complement-Mediated Bactericidal Activity of Human Antibodies in Poly W $\alpha 2 \rightarrow 8$ N-Acetylneuraminic Acid, the Capsular Polysaccharide of *Neisseria meningitidis* Serogroup B, *The Journal of Infectious Diseases* 172:1279-1289 (1995).
Michon et al., Conformational Differences Between Linear $\alpha(2 \rightarrow 8)$-Linked Homosialooligosaccharides and the Epitope of the Group B Meningococcal Polysaccharide, *Biochemistry* 26:8399-8405 (1987).
Moreno et al., *J. Gen. Microbiol.* 129:2451-2456 (1983).
Pizza et al., Identification of vaccine candidates against serogroup B Meningococcus by whole-genome sequencing, *Science* 287:1816-1820 (2000).
Pon et al., *J. Exp. Med.* 185:1929-1938 (1997).
Poolman, Jan T., Development of a Meningococcal Vaccine, *Infectious Agents and Disease* 4:13-28 (1995).
Raff et al., *J. Infect. Dis.* 157(1):118-126 (1988).
Rougon et al., *J. Cell. Biol.* 103:2429-2437 (1986).
Sato et al., *J. Biol. Chem.* 270:18923-18928 (1995).
Sukkonen et al., *Microbial. Pathogenesis* 1:101-105 (1986).
Tettelin et al., Complete genome sequence of *Neisseria meningitidis* serogroup B strain MC58, *Science* 287:1809-1815 (2000).
Tome et al., *Acta Pathol. Jpn.* 43:168-175 (1993).
Vaesen et al., *Biol. Chem. Hoppe. Seyler* 372:451-453 (1993).
Westerink et al., Development and Characterization of an Anti-Idiotype Antibody to the Capsular Polysaccharide of *Neisseria mengingitidis* Serogroup C, *Infection and Immunity* 56(5):1120-1127 (1988).
DataBase WPI., Novel Strain of *Neisseria meningitidis* Group Useful Produce Capsule Polysaccharide Protein Complex, Jan. 30, 1992.

\* cited by examiner

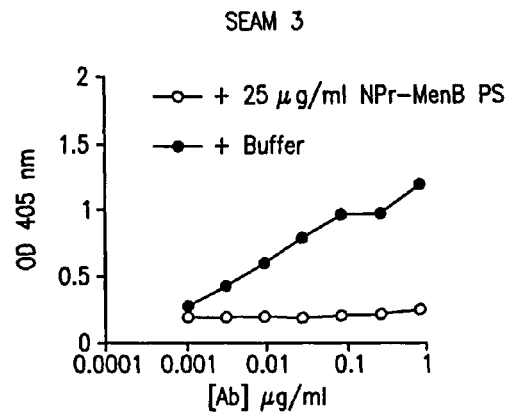
FIG. I-A
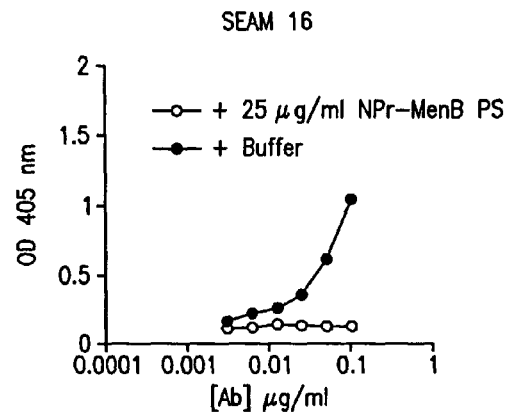
FIG. I-C
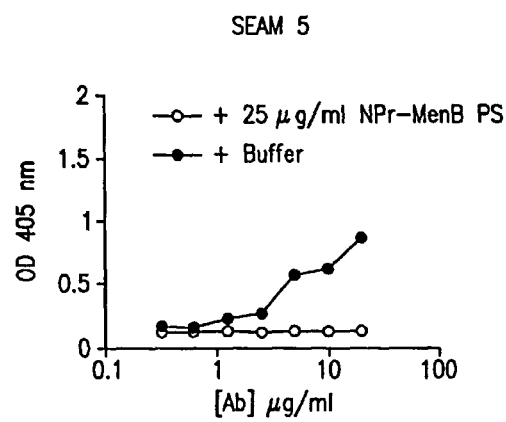
FIG. I-B
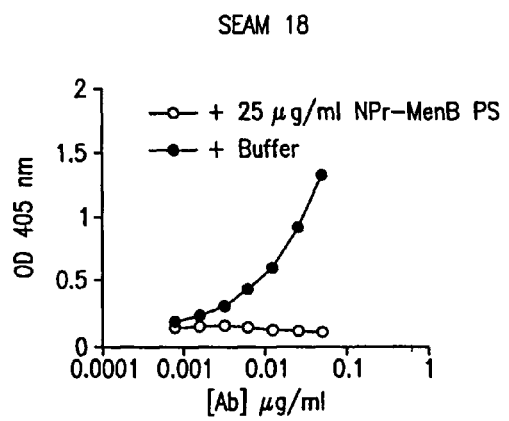
FIG. I-D

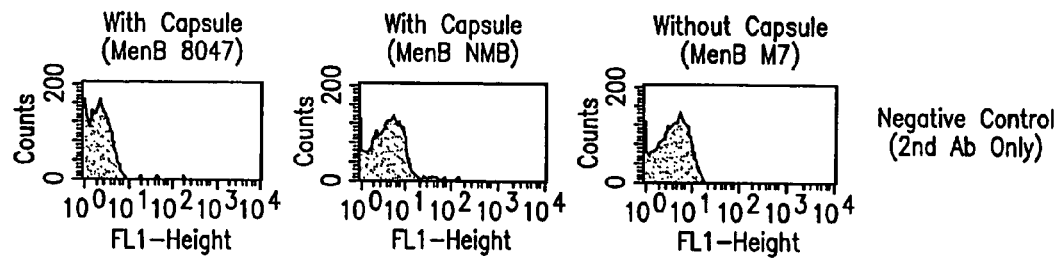
FIG. 4-A — Negative Control (2nd Ab Only)
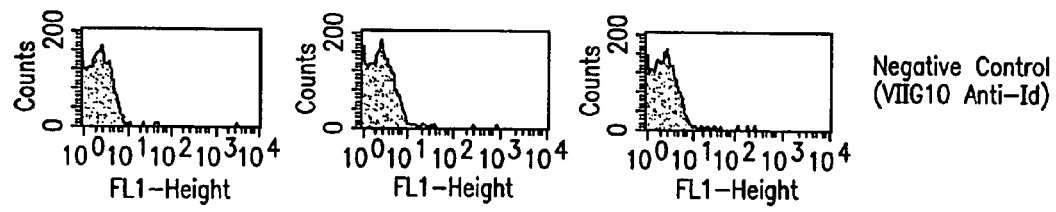
FIG. 4-B — Negative Control (VIIG10 Anti-Id)
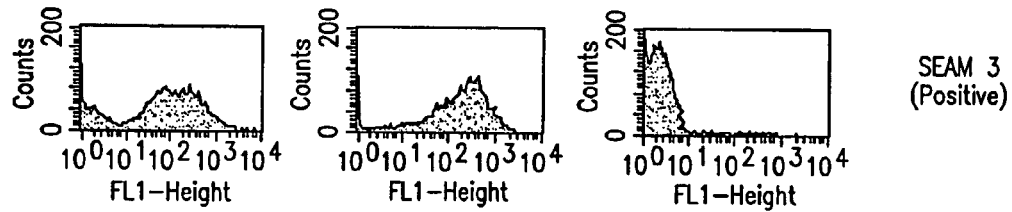
FIG. 4-C — SEAM 3 (Positive)
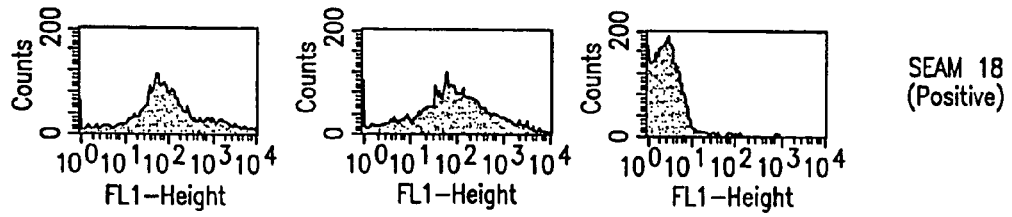
FIG. 4-D — SEAM 18 (Positive)

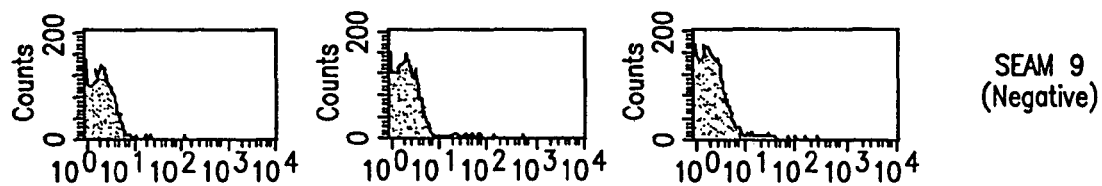
FIG. 4-E
SEAM 9 (Negative)
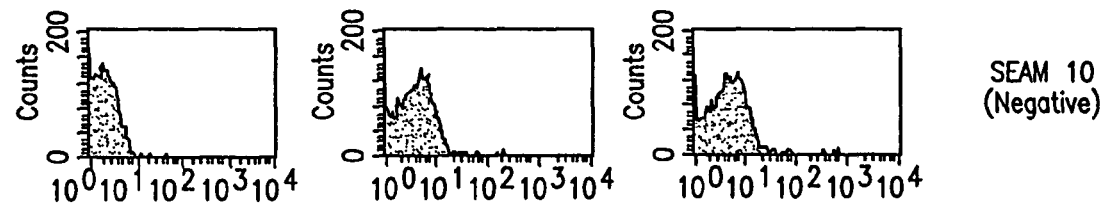
FIG. 4-F
SEAM 10 (Negative)
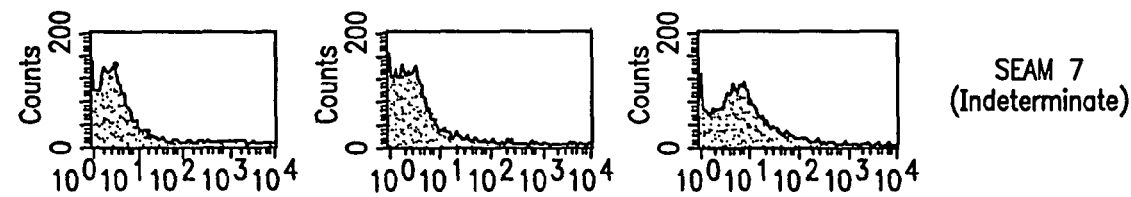
FIG. 4-G
SEAM 7 (Indeterminate)

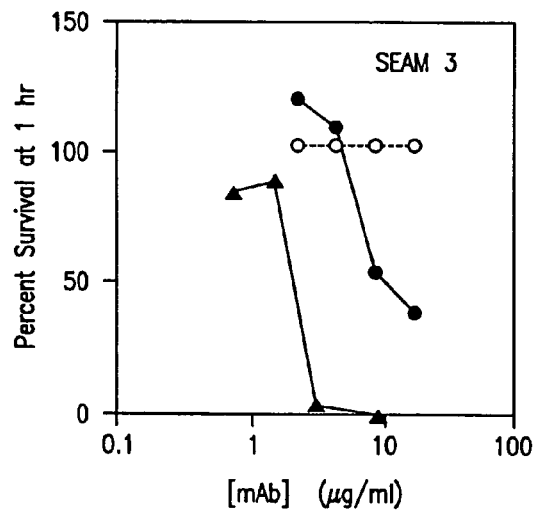
FIG. 5-A
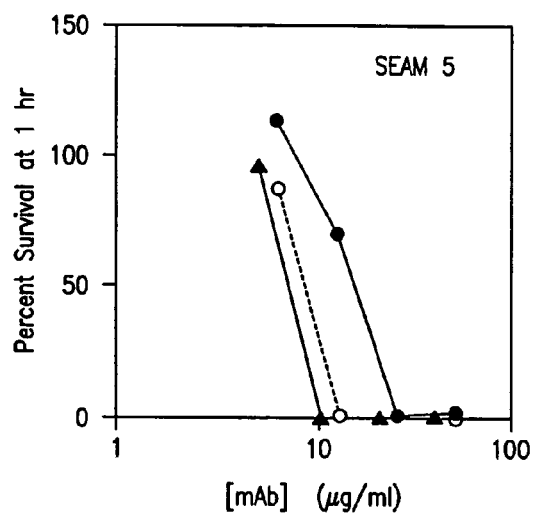
FIG. 5-B
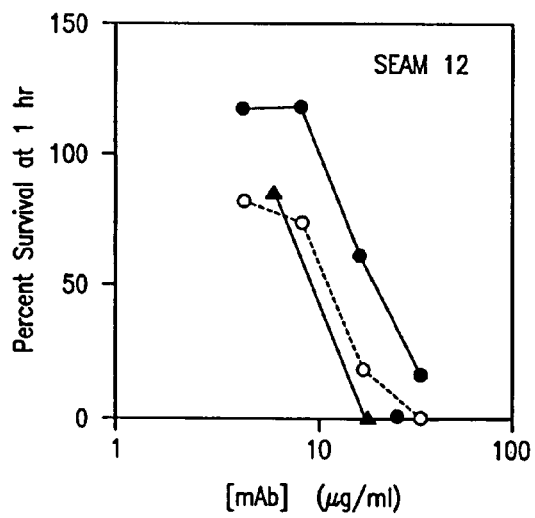
FIG. 5-C
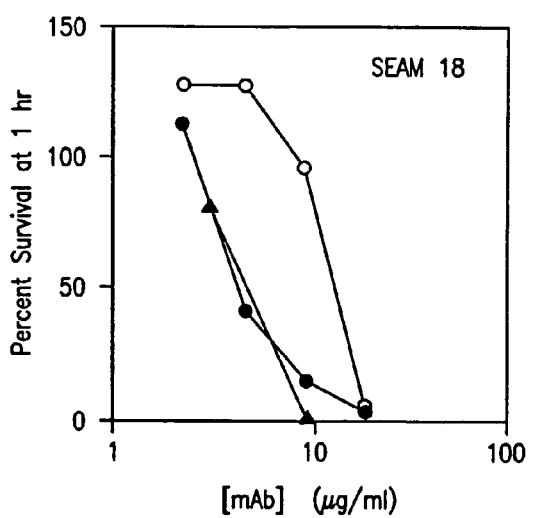
FIG. 5-D

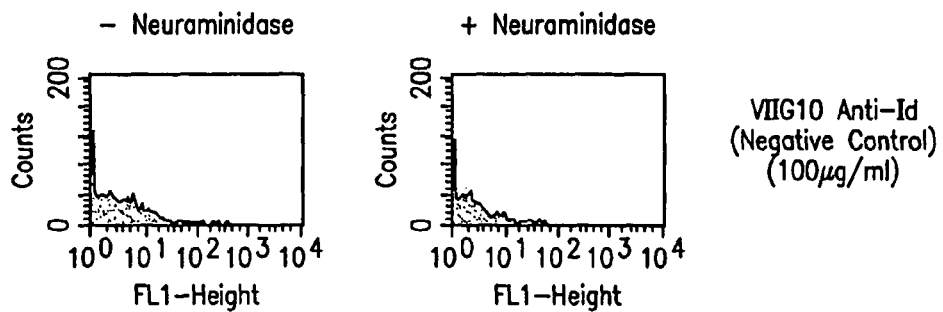
FIG. 6-A
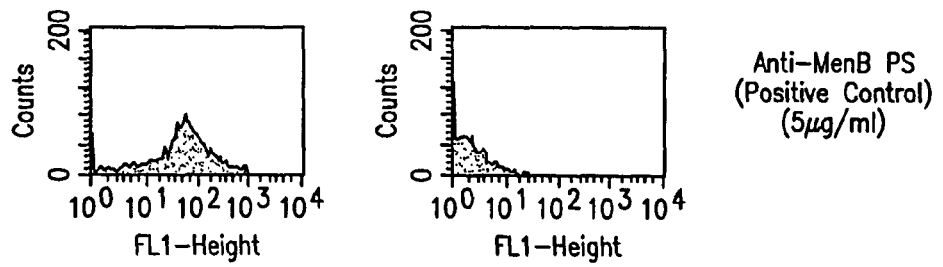
FIG. 6-B
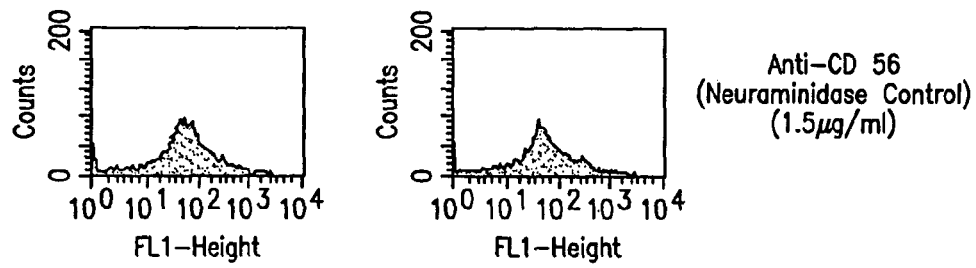
FIG. 6-C
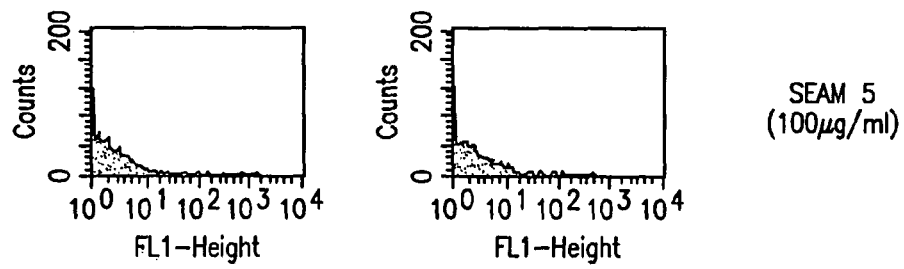
FIG. 6-D
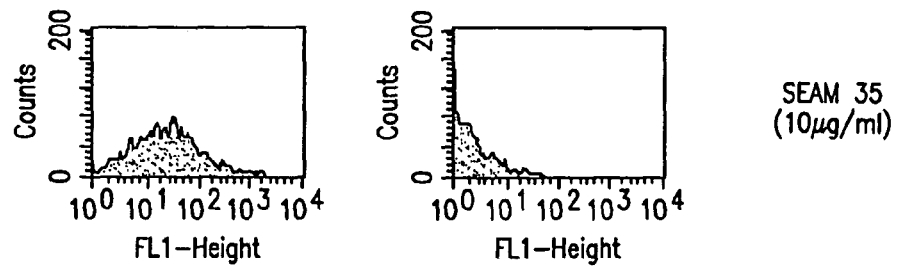
FIG. 6-E

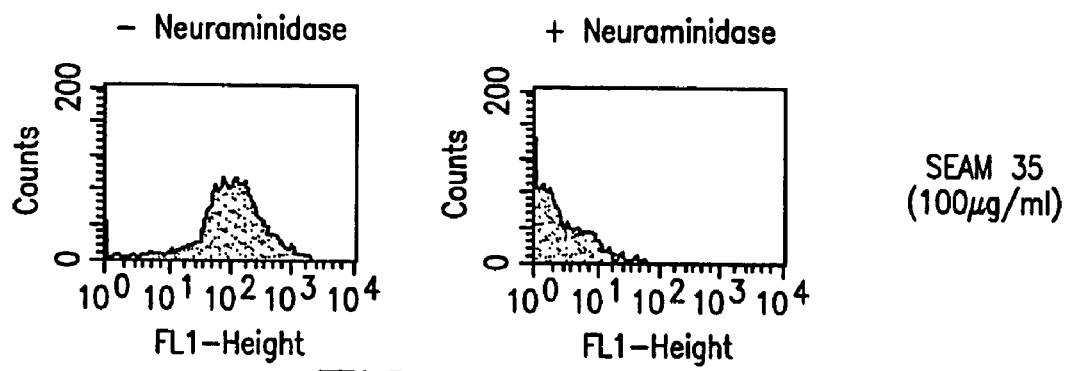
FIG. 6-F
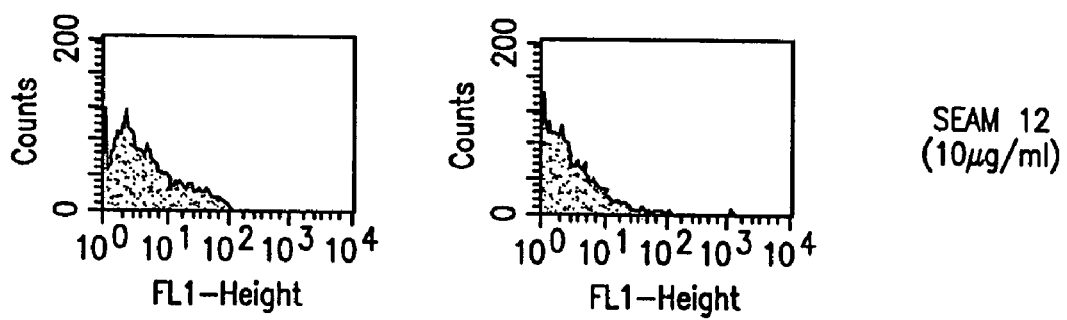
FIG. 6-G
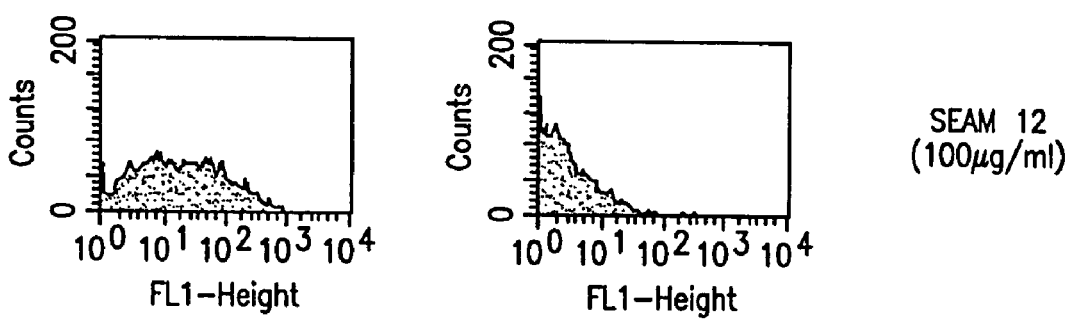
FIG. 6-H
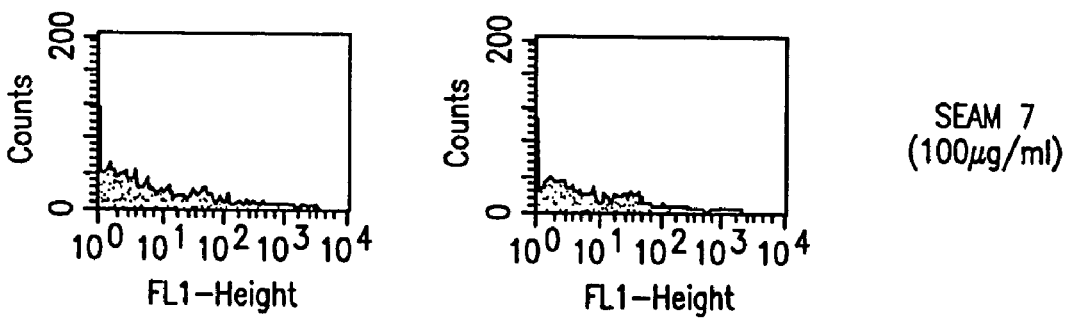
FIG. 6-I

| | | |
|---|---|---|
| Pep 1 | PRO-LEU-ARG-SER-LEU-ARG-SER-TYR-TRP | (SEQ ID NO. 1) |
| Pep 2 | SER-ASN-CYS-GLU-ILE-TRP-ARG-VAL-GLY-CYS | (SEQ ID NO. 2) |
| Pep 3 | CYS-MET-ARG-TYR-GLU-ALA-THR-CYS | (SEQ ID NO. 3) |
| Pep 4 | CYS-GLY-LEU-PRO-ARG-PHE-ARG-CYS | (SEQ ID NO. 4) |
| Pep 5 | TYR-CYS-GLN-ILE-GLN-GLY-SER-CYS | (SEQ ID NO. 5) |
| Pep 6 | GLN-VAL-PRO-CYS-SER-SER-ARG-ARG-GLY-CYS | (SEQ ID NO. 6) |
| Pep 7 | ARG-TYR-GLY-CYS-LEU-LEU-MET-ARG-GLY-CYS | (SEQ ID NO. 7) |
| Pep 8 | PHE-HIS-CYS-LYS-VAL-ASN-ARG-GLY-CYS | (SEQ ID NO. 8) |
| Pep 9 | SER-CYS-ARG-SER-LYS-ASN-SER-ALA-GLY-CYS | (SEQ ID NO. 9) |
| Pep 10 | THR-VAL-GLU-THR-VAL-GLU-SER-CYS | (SEQ ID NO. 10) |
| Pep 11 | TYR-GLN-GLY-PRO-LEU-GLY-TRP-ARG | (SEQ ID NO. 11) |
| Pep 12 | CYS-TRP-PRO-THR-LEU-GLU-GLY-CYS | (SEQ ID NO. 12) |
| Pep 13 | CYS-LEU-THR-SER-TRP-SER-SER-CYS | (SEQ ID NO. 13) |
| Pep 14 | CYS-GLY-LEU-GLU-LEU-GLN-GLY-CYS | (SEQ ID NO. 14) |
| Pep 15 | CYS-THR-THR-ILE-MET-CYS-SER-THR | (SEQ ID NO. 15) |
| Pep 16 | GLY-TYR-GLU-VAL-GLN-PRO-PHE-HIS | (SEQ ID NO. 16) |
| Pep 17 | VAL-ALA-LYS-THR-VAL-ARG-PRO-PRO | (SEQ ID NO. 17) |
| Pep 18 | TRP-ALA-SER-TRP-VAL-GLY-GLY-PRO | (SEQ ID NO. 18) |
| Pep 19 | ASP-ASP-GLY-TYR-GLU-ILE-ARG-TRP | (SEQ ID NO. 19) |
| Pep 20 | SER-ARG-MET-GLY-GLY-ARG-ARG | (SEQ ID NO. 20) |
| Pep 21 | HIS-ASN-LYS-SER-LYS-LEU-GLU-ALA | (SEQ ID NO. 21) |
| Pep 22 | GLY-HIS-GLY-ALA-TYR-THR-ARG-LEU | (SEQ ID NO. 22) |
| Pep 23 | LYS-SER-LEU-ASN-ALA-MET-VAL-LEU | (SEQ ID NO. 23) |
| Pep 24 | PRO-TRP-SER-ARG-LEU-LYS-SER-PRO | (SEQ ID NO. 24) |
| Pep 25 | PRO-SER-LYS-GLY-LYS-VAL-LEU-SER | (SEQ ID NO. 25) |
| Pep 26 | GLY-PRO-MET-SER-ILE-ASP-LEU-ARG | (SEQ ID NO. 26) |
| Pep 27 | ARG-THR-GLU-LEU-GLY-TRP-ARG-TYR | (SEQ ID NO. 27) |
| Pep 28 | SER-ASP-SER-GLY-CYS-TYR-GLY-TYR | (SEQ ID NO. 28) |
| Pep 29 | CYS-GLY-THR-GLN-HIS-VAL-GLY-CYS | (SEQ ID NO. 29) |
| Pep 30 | CYS-GLY-THR-HIS-ASP-LEU-ALA-CYS | (SEQ ID NO. 30) |
| Pep 31 | CYS-GLN-LYS-GLY-ALA-ARG-GLY-CYS | (SEQ ID NO. 31) |
| Pep 32 | CYS-SER-ARG-TYR-ASN-GLY-GLY-CYS | (SEQ ID NO. 32) |
| Pep 33 | CYS-GLY-ARG-SER-THR-GLU-LEU-CYS | (SEQ ID NO. 33) |
| Pep 34 | CYS-ARG-ASN-SER-GLN-GLY-TYR-CYS | (SEQ ID NO. 34) |
| Pep 35 | LEU-ASP-SER-GLN-LEU-ARG-ARG-THR | (SEQ ID NO. 35) |
| Pep 36 | GLY-TRP-LEU-PHE-ARG-GLY-LEU-MET | (SEQ ID NO. 36) |
| Pep 37 | LEU-ASN-PHE-LYS-VAL-ARG-HIS-ASN | (SEQ ID NO. 37) |
| Pep 38 | ALA-LYS-SER-VAL-HIS-TYR-GLY-ILE | (SEQ ID NO. 38) |
| Pep 39 | CYS-VAL-ALA-LEU-MET-GLY-GLY-CYS | (SEQ ID NO. 39) |
| Pep 40 | CYS-GLN-LYS-GLY-ALA-ARG-ALA-ARG-GLY-CYS | (SEQ ID NO. 40) |
| Pep 41 | PHE-ALA-ALA-ALA-LEU-GLY-GLN-ASN | (SEQ ID NO. 41) |
| Pep 42 | TYR-SER-HIS-TRP-LYS-TRP-ARG-TRP | (SEQ ID NO. 42) |
| Pep 43 | GLN-MET-ARG-PRO-ALA-LEU-ASN-SER | (SEQ ID NO. 43) |

FIG. 7-A

```
Pep 44   TRP-LEU-ASP-ARG-GLY-SER-THR-PRO                    (SEQ ID NO. 44)
Pep 45   ASP-TRP-ASP-ARG-ALA-VAL-VAL-LEU                    (SEQ ID NO. 45)
Pep 46   PHE-PRO-LEU-LEU-ARG-GLY-ALA-ARG                    (SEQ ID NO. 46)
Pep 47   PHE-ALA-TRP-SER-CYS-THR-TRP-PRO-GLY-CYS            (SEQ ID NO. 47)
Pep 48   LYS-LEU-HIS-VAL-GLY-PRO-ARG-ASN                    (SEQ ID NO. 48)
Pep 49   LEU-PHE-PRO-LYS-PRO-ARG-LEU-PRO                    (SEQ ID NO. 49)
Pep 50   TYR-LEU-GLY-THR-SER-ARG-ASN-GLY-LEU                (SEQ ID NO. 50)
Pep 51   CYS-GLY-THR-HIS-ASP-LEU-ALA-CYS                    (SEQ ID NO. 51)
Pep 52   CYS-GLY-SER-ALA-PHE-SER-ALA-HIS-PRO                (SEQ ID NO. 52)
Pep 53   SER-TRP-TRP-HIS-ASN-TYR-CYS-PRO-GLY-CYS            (SEQ ID NO. 53)
Pep 54   GLU-ARG-CYS-ALA-CYS-GLY-ARG-GLY-GLY-CYS            (SEQ ID NO. 54)
Pep 55   GLU-THR-LYS-GLU-ARG-GLY-GLU-SER-GLY-CYS            (SEQ ID NO. 55)
Pep 56   ALA-PHE-CYS-CYS-GLY-SER-GLY-THR-ARG-GLY-CYS        (SEQ ID NO. 56)
Pep 57   ALA-PHE-CYS-GLY-SER-GLY-THR-ARG-GLY-CYS            (SEQ ID NO. 57)
Pep 58   ASN-LEU-SER-SER-PRO-CYS-GLY-ARG-GLY-CYS            (SEQ ID NO. 58)
Pep 59   VAL-ALA-CYS-ARG-SER-GLY-MET-GLY-GLY-CYS            (SEQ ID NO. 59)
Pep 60   ILE-ARG-SER-GLY-CYS-ARG-PRO-VAL-GLY-CYS            (SEQ ID NO. 60)
Pep 61   CYS-TRP-LYS-PRO-GLY-ARG-SER-GLY-CYS                (SEQ ID NO. 61)
Pep 62   PHE-VAL-ARG-GLY-VAL-GLY-VAL-GLY-CYS                (SEQ ID NO. 62)
Pep 63   GLY-CYS-TRP-ARG-TRP-ILE-GLN-PRO-GLY-CYS            (SEQ ID NO. 63)
Pep 64   PHE-ALA-TRP-SER-CYS-THR-TRP-PRO-GLY-CYS            (SEQ ID NO. 64)
Pep 65   ARG-CYS-ARG-GLY-HIS-GLY-GLY-PRO-GLY-CYS            (SEQ ID NO. 65)
Pep 66   PHE-ALA-TRP-SER-CYS-THR-TRP-PRO-GLY-CYS            (SEQ ID NO. 66)
Pep 67   CYS-ASN-LEU-ARG-MET-SER-SER-ALA-GLY-CYS            (SEQ ID NO. 67)
```

FIG. 7-B

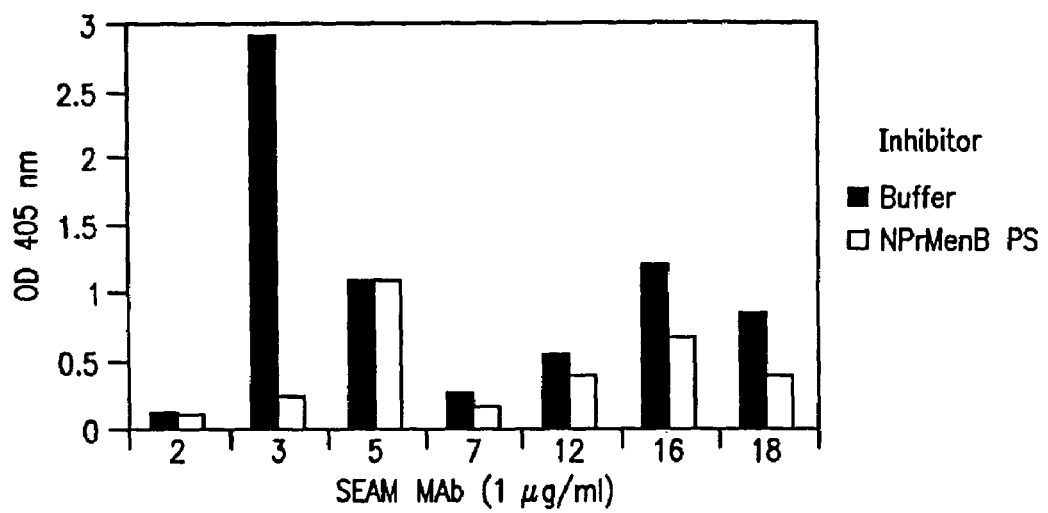
FIG. 8-A
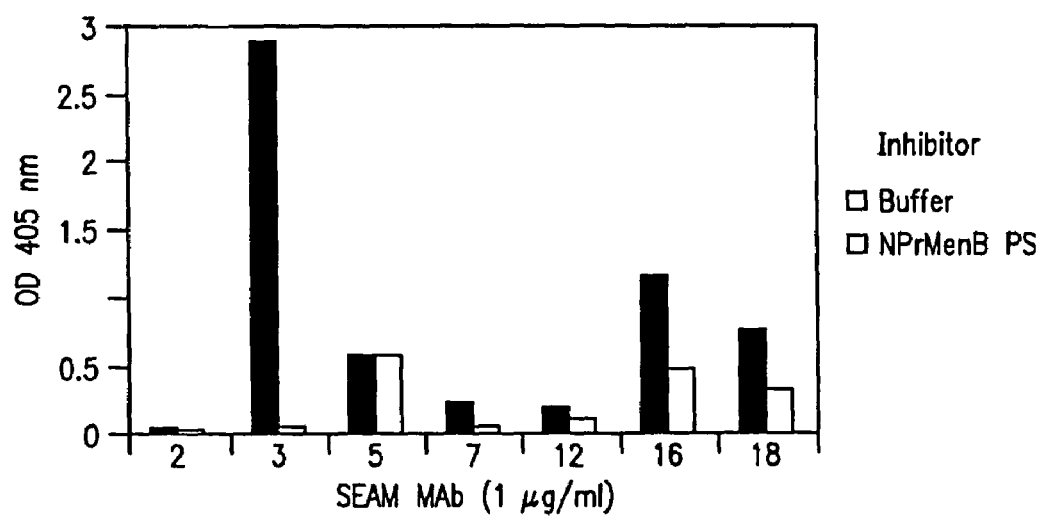
FIG. 8-B

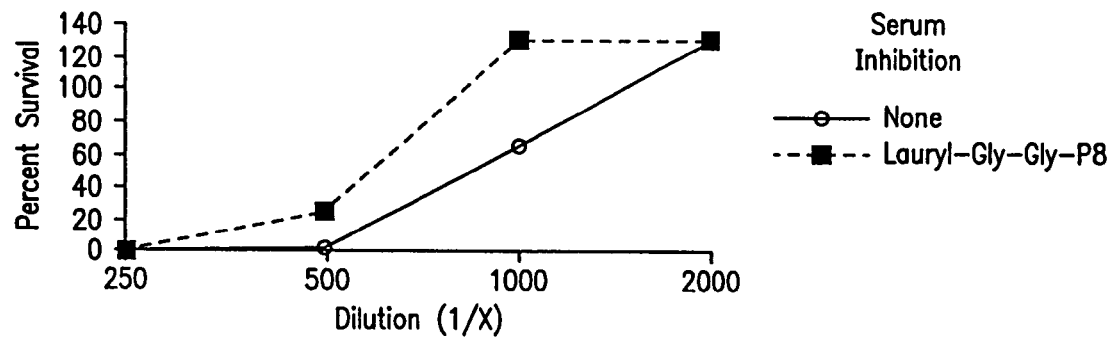
FIG. 12-A
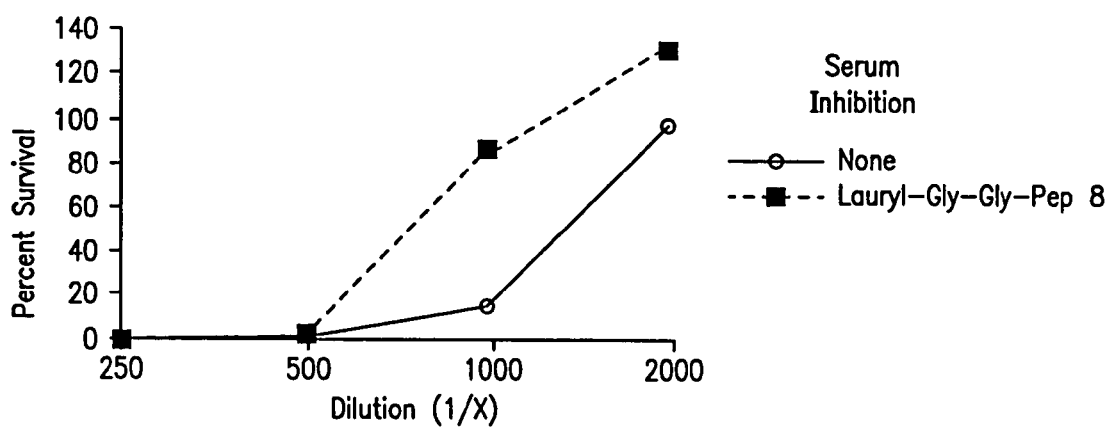
FIG. 12-B

METHODS FOR ISOLATING MOLECULAR MIMETICS OF UNIQUE *NEISSERIA MENINGITIDIS* SEROGROUP B EPITOPES

CROSS-REFERENCE TO RELATED APPLICATION

This application is a divisional of U.S. patent application Ser. No. 09/910,552, filed Jul. 23, 2001, now U.S. Pat. No. 6,642,354, which is a divisional of U.S. patent application Ser. No. 09/494,822, filed Jan. 31, 2000, now abandoned, which is a continuation of U.S. patent application Ser. No. 08/925,002, filed Aug. 27, 1997, now U.S. Pat. No. 6,048,527, from which applications priority is claimed pursuant to 35 U.S.C. §120; and is related to provisional patent application Ser. No. 60/025,799, filed Aug. 27, 1996, from which application priority is claimed under 35 U.S.C. §119(e)(1) and which applications are incorporated herein by reference in their entireties.

TECHNICAL FIELD

The present invention pertains generally to bacterial pathogens. In particular, the invention relates to antibodies that elicit functional activity against *Neisseria meningitidis* serogroup B and also lack autoimmune activity, methods of obtaining and using the same, as well as molecular mimetics identified using the antibodies.

BACKGROUND OF THE INVENTION

*Neisseria meningitidis* is a causative agent of bacterial meningitis and sepsis. *Meningococci* are divided into serological groups based on the immunological characteristics of capsular and cell wall antigens. Currently recognized serogroups include A, B, C, D, W-135, X, Y, Z and 29E. The polysaccharides responsible for the serogroup specificity have been purified from several of these groups, including A, B, C, D, W-135 and Y.

*N. meningitidis* serogroup B ("MenB") accounts for approximately 50 percent of bacterial meningitis in infants and children residing in the U.S. and Europe. The organism also causes fatal sepsis in young adults. In adolescents, experimental MenB vaccines consisting of outer membrane protein (OMP) vesicles have been found to be approximately 50% protective. However, no protection has been observed in vaccinated infants and children, the age groups at greatest risk of disease. Additionally, OMP vaccines are serotype- and subtype-specific, and the dominant MenB strains are subject to both geographic and temporal variation, limiting the usefulness of such vaccines.

Effective capsular polysaccharide-based vaccines have been developed against meningococcal disease caused by serogroups A, C, Y and W135. However, similar attempts to develop a MenB polysaccharide vaccine have failed due to the poor immunogenicity of the capsular MenB polysaccharide (termed "MenB PS" herein). MenB PS is a homopolymer of (N-acetyl ($\alpha 2 \rightarrow 8$) neuraminic acid. *Escherichia coli* K1 has the identical capsular polysaccharide. Antibodies elicited by MenB PS cross-react with host polysialic acid (PSA). PSA is abundantly expressed in fetal and newborn tissue, especially on neural cell adhesion molecules ("NCAMs") found in brain tissue. PSA is also found to a lesser extent in adult tissues including in kidney, heart and the olfactory nerve. Thus, most anti-MenB PS antibodies are also autoantibodies. Such antibodies therefore have the potential to adversely affect fetal development, or to lead to autoimmune disease.

MenB PS derivatives have been prepared in an attempt to circumvent the poor immunogenicity of MenB PS. For example, $C_3$–$C_8$ N-acyl-substituted MenB PS derivatives have been described. See, EP Publication No. 504,202 B, to Jennings et al. Similarly, U.S. Pat. No. 4,727,136 to Jennings et al. describes an N-propionylated MenB PS molecule, termed "NPr-MenB PS" herein. Mice immunized with NPr-MenB PS glycoconjugates were reported to elicit high titers of IgG antibodies. Jennings et al. (1986) *J. Immunol.* 137: 1708. In rabbits, two distinct populations of antibodies, purportedly associated with two different epitopes, one shared by native MenB PS and one unshared, were produced using the derivative. Bactericidal activity was found in the antibody population that did not cross react with MenB PS. Jennings et al. (1987) *J. Exp. Med.* 155:1207. The identity of the bacterial surface epitope(s) reacting with the protective antibodies elicited by this conjugate remains unknown.

Peptides can serve as mimics of polysaccharides by binding to polysaccharide-specific antibodies as well as to other polysaccharide binding proteins. For example, concanavalin A (Con A), which binds to oligosaccharides bearing terminal alpha-linked mannose or glucose residues, has been used to select peptide mimetics from random libraries of bacterial phage bearing short peptide sequences at the amino-terminus of the pIII coat protein. Olderberg et al. (1992) *Proc. Natl. Acad. Sci. USA* 89:5393, Scott et al. (1992) *Proc. Natl. Acad. Sci. USA* 89:5398. Similarly, monoclonal antibodies have identified peptide mimetics of a carbohydrate present on the surface of adinocarcinona cells from a phage library Hoess at al. (1993) *Gene* 128:43.

Peptides can also elicit polysaccharide-specific antibodies. For example, Westerink et al. (1988) *Infect. Immun.* 56:1120, used a monoclonal antibody to the *N. meningitidis* serogroup C ("MenC") capsular ploysacceride to elicit an anti-idiotype antibody. Mice immuniced with the anti-idiotype antibody were protected against infection with a lethal dose of MenC bacteria. These experimenters subsequently demonstrated that a peptide fragment of a MenC anti-idiotype antibody eliciten serum anti-MenC antibodies and protected animals from bacteremia and death after lethal challenge with MenC bacteria. Wescerink et al. (1995) *Proc. Natl. Acad. Sci USA* 92:4021.

However, to date, no such approach has been taken with respect to MenB vaccine development. It is readily apparent that the production of a safe and effective vaccine against MenB would be particularly desirable.

SUMMARY OF THE INVENTION

The present invention is based on the discovery of functionally active antibodies directed against MenB PS derivatives, wherein the antibodies do not cross-react, on are minimally cross-reactive, with host tissues as determined using the assays described herein. These antibodies therefore pose minimal risk of evoking autoimmune disease and are termed "non-autoreactive" herein. Assays used herein to determine autoreactivity include binding assays against a neuroblastoma cell line expressing long chain polysiatic acid residues on the cell surface. Specifically, antibodies that are negative in these assays are considered to lack autoreactivity. The non-autoreactive antibodies are particularly useful for identifying molecular mimetics of unique MenB PS epitopes that can be used in vaccine compositions. Furthermore, the antibodies humanized versions of the antibodies fragments and functional equivalents thereof, will also and use in passive immunization against, and/or to a adjunct to therapy for, MenB and *E. coli* K1 disease Since such molecules do not bind to polysialic acid in tissues as determined by the autoreactivity assays described herein, they provide a safe and efficacious method for the treatment and/or prevention of MenB and *E. coli* K1 disease.

Accordingly, in one embodiment, the subject invention relates to antibodies directed against MenB PS derivatives, wherein the antibodies are not autoreactive with host tissue. Such antibodies may further be characterized as being capable of eliciting functional activity against MenB bacteria. One particular group of such antibodies is also characterized as non cross-reactive with *Neisseria meningitidis* serogroup B capsular polysaccharide (NAc-MenB PS) in an ELISA. However, these antibodies are anti-capsular in that they can bind to the cell surface of a Group B encapsulated bacteria, but not to capsular-deficient mutants.

Another embodiment of the invention relates to monoclonal antibodies directed against MenB PS derivatives, and hybridomas producing those monoclonal antibodies.

Other embodiments of the invention relate to unique *Neisseria meningitidis* serogroup B epitopes that are capable of being bound by the antibody molecules of the present invention.

Still further embodiments of the subject invention are related to methods for isolating molecular mimetics of unique epitopes of MenB PS and molecular mimetics identified using the methods. The methods comprise:

(a) providing a population of molecules including a putative molecular mimetic of a unique epitope of MenB PS;

(b) contacting the population of molecules with the antibodies described above under conditions that allow immunological binding between the antibody and the molecular mimetic, if present, to provide a complex; and (c) separating the complexes from non-bound molecules.

In another embodiment, the subject invention is directed to a vaccine composition comprising a unique epitope of MenB in combination with a pharmaceutically acceptable excipient.

In yet another embodiment, the invention is directed to a vaccine composition comprising a molecular mimetic of a unique epitope of MenB in combination with a pharmaceutically acceptable excipient.

In still a further embodiment, the invention is directed to a vaccine composition comprising an anti-idiotypic antibody molecular mimetic of a unique epitope of MenB in combination with a pharmaceutically acceptable excipient.

In yet further embodiments, the invention relates to pharmaceutical compositions comprising the antibodies described above.

In another embodiment, the subject invention is directed to a method for treating or preventing MenB and/or *E. coli* K1 disease in a mammalian subject comprising administering an effective amount of the above pharmaceutical compositions to the subject.

These and other embodiments of the present invention will readily occur to those of ordinary skill in the art in view of the disclosure herein.

BRIEF DESCRIPTION OF THE FIGURES

FIGS. 1A–1D depict dose-response binding activity of three representative anti-NPr-MenB PS monoclonal antibodies (SEAM-3, SEAM-5, SEAM-16 and SEAM-18, respectively), to solid phase NPr-MenB PS as determined by ELISA. Data shown are for the antibodies diluted in buffer ( ), or in buffer containing 25 μg/ml of soluble NPr-MenB PS (○). Different ranges for the X axis in the data are used, wherein monoclonal antibodies SEAM-3, SEAM-16, and SEAM-18 are shown at 0.0001 to 1 μg/ml, and monoclonal antibody SEAM-5 is shown at 0.1 to 100 μg/ml.

FIG. 2 depicts the inhibition of binding of four representative anti-NPr-MenB PS monoclonal antibodies (SEAM-2, SEAM-3, SEAM-16 and SEAM-18) to solid phase NPr-MenB PS by either 25 μg/ml of soluble high molecular weight (HMW) NPr-MenB PS inhibitor (■), or 25 μg/ml of low molecular weight (LMW) NPr-MenB oligosaccharide inhibitor having an average degree of polymerization of 3.8 monomers (□), as determined by ELISA.

FIG. 3 depicts the binding of five representative anti-NPr-MenB PS monoclonal antibodies (SEAM-12, SEAM-16, SEAM-18, SEAM-2, and SEAM-3) to solid phase NAc-MenB PS as determined by ELISA. Three of the antibodies, SEAM-12, SEAM-16 and SEAM-18, showed significant binding when tested at 0.5 and/or 5 μg/ml of antibody. Two other antibodies, SEAM-2 and SEAM-3, were negative when tested at 5-fold higher concentrations (25 μg/ml of antibody).

FIGS. 4A–4G depict the cross-reactivity of control antibodies and representative anti-NPr-MenB PS monoclonal antibodies (SEAM-3, SEAM-18, SEAM-9, SEAM-10, and SEAM-7) with encapsulated and non-encapsulated whole MenB bacteria as determined by indirect fluorescence flow cytometry. The capsule contains NAc-MenB PS.

FIGS. 5A–5D depict the complement-mediated bactericidal activity of four representative anti-NPr-MenB PS monoclonal antibodies (SEAM-3, SEAM-5, SEAM-12, and SEAM-18, respectively) when tested against the MenB test strain 8047. Results are shown from experiments with three different complement sources: infant rabbit complement I (▲); infant rabbit complement II ( ); and human complement (o).

FIGS. 6A–6I depict the cross-reactivity of three control antibodies and four representative anti-NPr-MenB PS monoclonal antibodies (SEAM-5, SEAM-35, SEAM-12, and SEAM-7) with polysialic acid antigens displayed on the surface of the human neuroblastoma cell line CHP-134 as determined by indirect fluorescence flow cytometry.

FIGS. 7A–7B depict the amino acid sequences of 67 unique peptide mimetic sequences (SEQ ID NOs. 1–67) selected by SEAM monoclonal antibodies from phage display peptide libraries.

FIGS. 8A and 8B depict the ELISA binding activity of seven representative SEAM monoclonal antibodies (SEAM-2, SEAM-3, SEAM-5, SEAM-7, SEAM-12, SEAM-16, and SEAM-18) to two peptides containing peptide mimetic sequences selected by SEAM monoclonal antibodies. (In FIG. 8A, "Pep 4" is Lauryl-GLY-GLY-[SEQ ID NO. 4]-Amide, and in FIG. 8B, "Pep 8" is Lauryl-GLY-GLY-[SEQ ID NO. 8]-Amide). Each peptide contains a carboxyl terminal amide and a Lauryl-Gly-Gly at the amino terminal end in order to facilitate binding of the peptide to the microtiter plate.

FIG. 9 depicts the antibody binding activity of pooled (four mice per pool) immune and unimmunized (CTL) sera from CD1 mice as measured by an ELISA with peptide Pep 8 as the solid phase antigen. The immune sera were from mice immunized with 5 μg or 50 μg of mimetic peptides complexed to the capsule-deficient *Neisseria meningitidis* Strain M7 outer membrane protein vesicles. The peptides included Pep 5 (Lauryl-GLY-GLY-[SEQ ID NO. 5]-Amide), Pep 8 (Lauryl-GLY-GLY-[SEQ ID NO. 8]-Amide), or a mixture of nine peptides Pep 1 through Pep 9 (Pep 1, Lauryl-GLY-GLY-[SEQ ID NO. 1]-Amide; Pep 2, Lauryl-GLY-GLY-[SEQ ID NO. 2]-Amide; Pep 3, Lauryl-GLY-GLY-[SEQ ID NO. 3]-Amide; Pep 4, Lauryl-GLY-GLY-

[SEQ ID NO. 4]-Amide; Pep 5, Lauryl-GLY-GLY-[SEQ ID NO. 5]-Amide; Pep 6, Lauryl-GLY-GLY-[SEQ ID NO. 6]-Amide; Pep 7, Lauryl-GLY-GLY-[SEQ ID NO. 7]-Amide; Pep 8, Lauryl-GLY-GLY-[SEQ ID NO. 8]-Amide; and Pep 9, Lauryl-GLY-GLY-[SEQ ID NO. 9]-Amide). Binding is compared between sera diluted in buffer (□), buffer containing soluble Pep 8 (Acetyl-[SE ID NO. 8]-Amide) (■), or buffer containing a soluble irrelevant peptide R1 (Acetyl-GLN-TRP-GLU-ARG-THR-TYR-Amide (SEQ ID NO. 68)) (cross-hatched bars).

Figure 9:
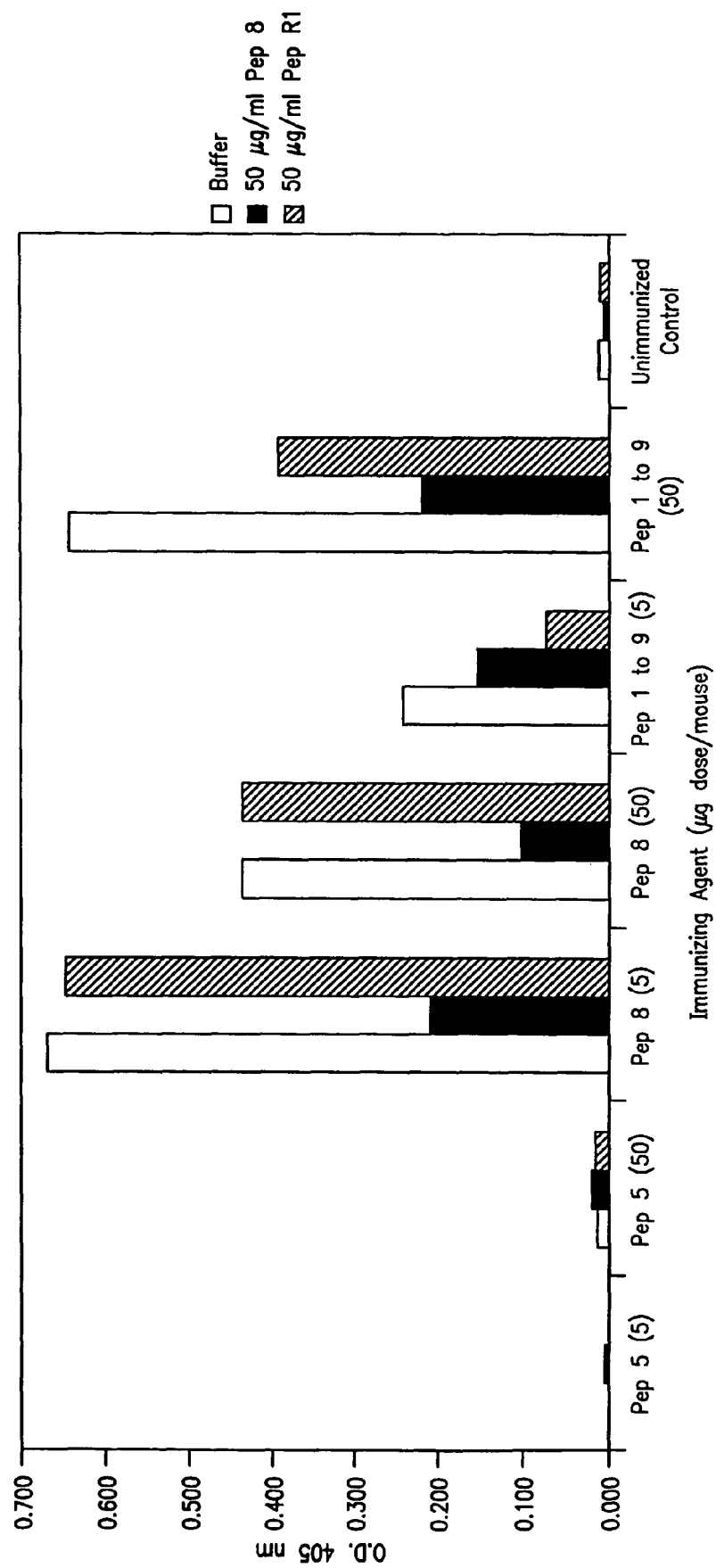
Figure 10:
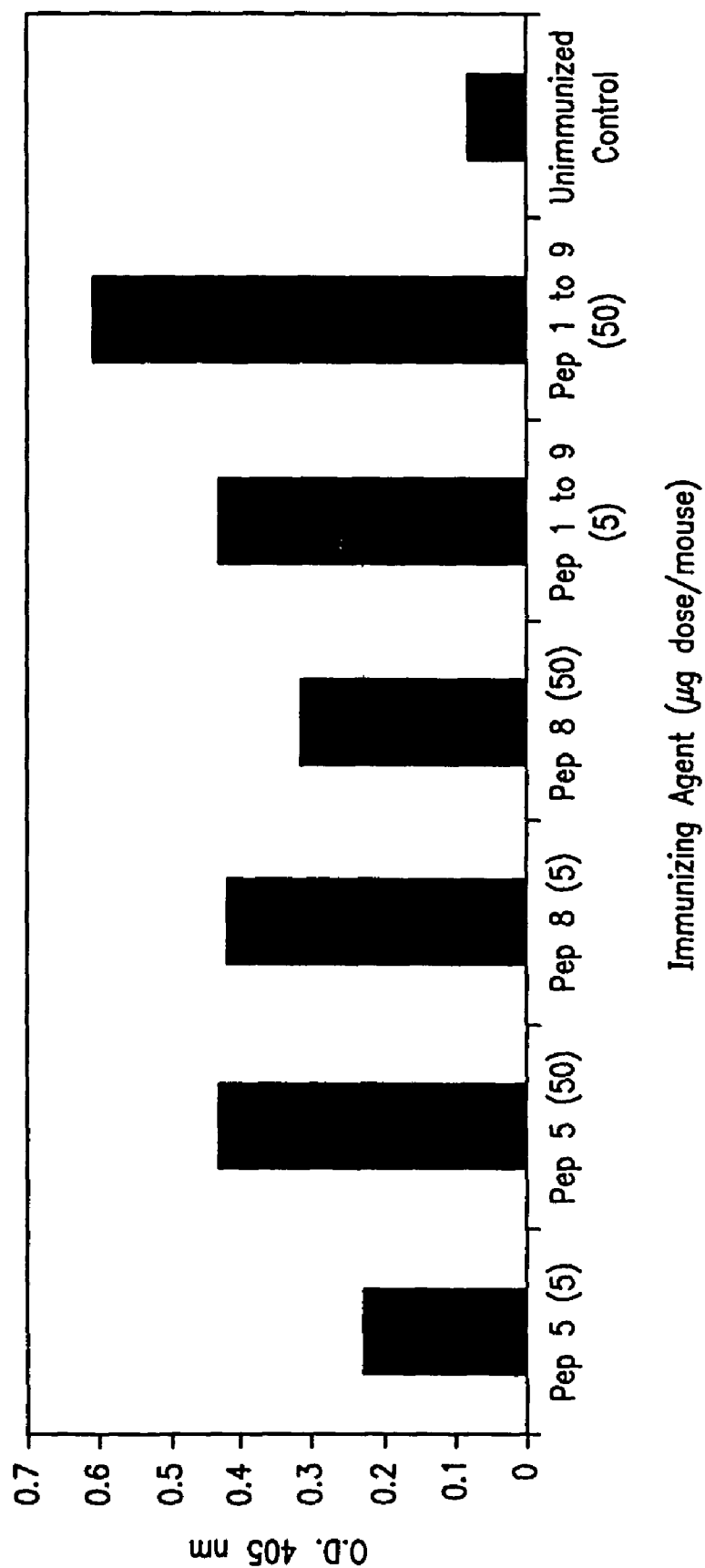

FIG. 10 depicts the antibody binding activity of pooled (four mice per pool) immune and unimmunized control sera from CD1 mice as measured by an ELISA with NPr-MenB PS as the solid phase antigen. The mice were immunized with the peptide immunogens as described above in FIG. 9.

Figure 11:
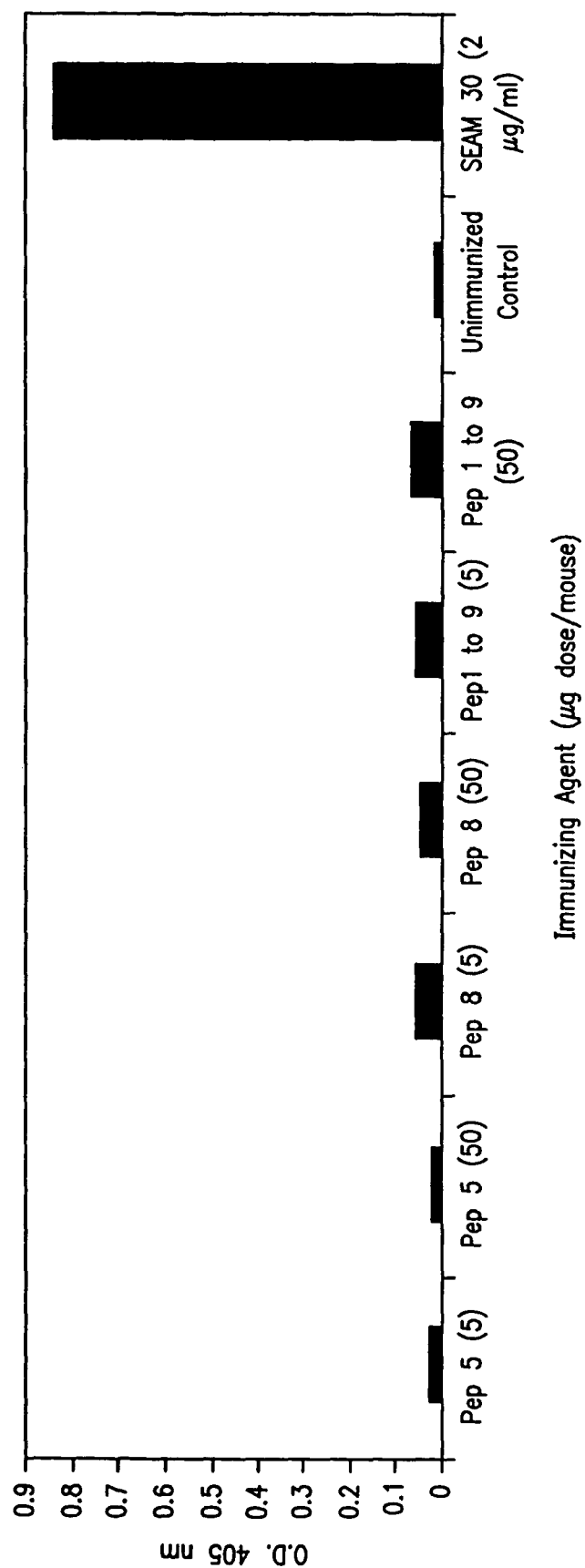

FIG. 11 depicts the antibody binding activity of pooled (four mice per pool) immune and unimmunized control sera from CD1 mice as measured by an ELISA with NAc-MenB PS as the solid phase antigen. The mice were immunized with the peptide immunogens as described above in FIG. 9. The SEAM-30 antibody, with known autoantibody activity, served as the positive control.

FIGS. 12A–12B depict the percent survival of bacteria incubated with various dilutions of test sera and human complement. The data shown are from testing pooled sera (four mice per pool) from CD1 mice immunized with 5 μg (FIG. 11A) or 50 μg (FIG. 11B) of mimetic peptide Pep 8 (Lauryl-GLY-GLY-[SEQ ID NO. 8]-Amide) complexed to capsular-deficient Neisseria meningitidis Strain M7 outer membrane protein vesicles. The sera were diluted in buffer, or in buffer containing Pep 8 inhibitor (100 μg/ml). The source of complement was human agammaglobulinemia and the bacterial test strain was 8047.

DETAILED DESCRIPTION OF THE INVENTION

The practice of the present invention will employ, unless otherwise indicated, conventional methods of immunology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

As used herein, a "MenB PS derivative" refers to a molecule obtained by the chemical modification of the native capsular polysaccharide of MenB. Such MenB PS derivatives include, but are not limited to, MenB PS molecules which have been modified by the substitution of sialic acid residue N-acetyl groups of the native molecule with appropriate acyl groups, such as $C_3$–$C_8$, and higher, acyl groups wherein the term "acyl group" encompasses any acylated linear, branched, aliphatic or aromatic molecule. A particularly preferred MenB PS derivative for use herein comprises the substitution of N-propionyl groups for N-acetyl groups of native MenB PS (termed "NPr-MenB PS" herein). Methods for synthesizing N-acyl-substituted MenB PS derivatives, including NPr-MenB PS, are known in the art and described in e.g., U.S. Pat. No. 4,727,136 to Jennings et al. and EP Publication No. 504,202 B, also to Jennings et al.

"Molecular mimetics" of MenB PS, or derivatives of MenB PS are molecules that functionally mimic at least one "unique" epitope expressed on a MenB bacteria. A "unique epitope" is an epitope capable of eliciting the formation of functionally active (e.g., opsonic and/or complement-mediated bactericidal) anti-MenB antibodies that either are not cross-reactive with polysialic acid in host tissue and hence lack autoimmune activity, or are minimally cross-reactive. Such molecular mimetics are useful in vaccine compositions and in eliciting antibodies for diagnostic or therapeutic applications, as described further below. Molecular mimetics include, but are not limited to, small organic compounds; nucleic acids and nucleic acid derivatives; saccharides or oligosaccharides; peptide mimetics including peptides, proteins, and derivatives thereof, such as peptides containing non-peptide organic moieties, synthetic peptides which may or may not contain amino acids and/or peptide bonds, but retain the structural and functional features of a peptide ligand, and peptoids and oligopeptoids which are molecules comprising N-substituted glycine, such as those described by Simon et al. (1992) *Proc. Natl. Acad. Sci. USA* 89:9367; and antibodies, including anti-idiotype antibodies. Methods for the identification and production of molecular mimetics are described more fully below.

The term "antibody" encompasses polyclonal and monoclonal antibody preparations, as well as preparations including hybrid antibodies, altered antibodies, F(ab')$_2$ fragments, F(ab) molecules, Fv fragments, single domain antibodies, chimeric antibodies and functional fragments thereof which exhibit immunological binding properties of the parent antibody molecule.

As used herein, the term "monoclonal antibody" refers to an antibody composition having a homogeneous antibody population. The term is not limited by the manner in which it is made. The term encompasses whole immunoglobulin molecules, as well as Fab molecules, F(ab')$_2$ fragments, Fv fragments, and other molecules that exhibit immunological binding properties of the parent monoclonal antibody molecule. Methods of making polyclonal and monoclonal antibodies are known in the art and described more fully below.

An "antigen" is defined herein to include any substance that may be specifically bound by an antibody molecule. An "immunogen" is an antigen that is capable of initiating lymphocyte activation resulting in an antigen-specific immune response.

By "epitope" is meant a site on an antigen to which specific B cells and T cells respond. The term is also used interchangeably with "antigenic determinant" or "antigenic determinant site." A peptide epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance spectroscopy. Furthermore, the identification of epitopes in a given protein is readily accomplished using techniques well known in the art. See, e.g., Geysen et al. (1984) *Proc. Natl. Acad. Sci. USA* 81:3998 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) *Molecular Immunology* 23:709 (technique for identifying peptides with high affinity for a given antibody). Antibodies that recognize the same epitope can be identified in a simple immunoassay showing the ability of one antibody to block the binding of another antibody to a target antigen.

A "unique MenB epitope" is defined herein as an epitope present on a MenB bacterium, wherein antibodies directed toward the epitope are capable of binding specifically to MenB and not cross reacting, or minimally cross reacting, with sialic acid residues present on the surface of host tissue. Immunogens containing or mimicking one or more "unique MenB epitopes" are thus useful in vaccines for prevention of MenB disease, and will not elicit an autoimmune response, or pose minimal risk of eliciting an autoimmune response.

An antibody displays "functional activity" against a MenB organism when the antibody molecule exhibits complement-mediated bactericidal activity and/or opsonic activity against MenB as determined using the assays described herein.

An antibody specific for a "unique" MenB epitope "lacks autoimmune activity," and/or is "not autoreactive" when the subject antibody does not exhibit cross-reactive immunological binding properties with polysialic acid in host tissue as determined using the binding assays described herein.

An antibody specific for a "unique" MenB epitope is "not autoreactive" when the subject antibody requires approximately ten times greater antibody concentration to exhibit binding to polysialic acid in host tissues, compared to a known cross-reactive auto antibody considered positive in the binding assays described herein. (For example, compare binding of SEAM-12 to binding of SEAM-35 in FIG. 6). Thus, the term encompasses those antibodies that are not autoreactive or minimally autoreactive in the binding assays described herein.

As used herein, the terms "immunological binding," and "immunological binding properties" refer to non-covalent interactions of the type which occur between an immunoglobulin molecule and an antigen for which the immunoglobulin is specific.

By "purified" and "isolated" is meant, when referring to a polypeptide, antibody or nucleotide sequence, that the indicated molecule is present in the substantial absence of other biological macromolecules of the same type. The terms "purified" and "isolated" as used herein preferably mean at least 75% by weight, more preferably at least 85% by weight, more preferably still at least 95% by weight, and most preferably at least 98% by weight, of biological macromolecules of the same type are present. Similarly, an "isolated" antibody is an antibody separated from a mixed population of antibodies, such as from antisera raised against a molecule of interest.

"Homology" refers to the percent of identity between two polynucleotide or polypeptide moieties. The correspondence between two or more sequences can be determined by techniques known in the art. For example, homology can be determined by a direct comparison of the sequence information between two polypeptide molecules. Two peptide sequences are "substantially homologous" when at least about 60% (preferably at least about 80%, and most preferably at least about 90%) of the amino acids match.

II. Modes of Carrying Out the Invention

The present invention is based on the discovery of novel functional antibodies directed against MenB. The antibodies do not cross-react, or are minimally cross-reactive with polysialic acid in host tissue as determined using the assays described herein, and hence the antibodies have a lower risk of evoking autoimmune activity than antibodies that are highly cross-reactive with host tissue. The antibodies can be used to identify molecular mimetics of unique epitopes found on the surface of MenB. The antibodies and/or mimetics can be used in vaccine compositions to treat and/or prevent MenB and *E. coli* K1 disease, as well as in diagnostic compositions for the identification of MenB and *E. coli* K1 bacteria.

As explained above, the native capsular polysaccharide of MenB, termed "MenB PS" herein, is poorly immunogenic in humans and other mammalian subjects. Furthermore, native MenB PS can elicit the production of autoantibodies and, hence, may be inappropriate for use in vaccine compositions. Thus, the present invention uses antibodies prepared against MenB PS derivatives. These antibodies are selected based on their ability to exhibit functional activity against MenB bacteria, wherein the functional activity is important in conferring protection against MenB disease. The antibodies are also selected on the basis of showing minimal or undetectable autoimmune activity.

More particularly, MenB PS derivatives were prepared for use in obtaining the antibody molecules of the present invention. The derivatives generally comprise $C_3$–$C_8$ acyl substitutions of sialic acid residue N-acetyl groups of the native molecule. Particularly preferred MenB PS derivatives comprise the substitution of N-propionyl groups for N-acetyl groups of native MenB PS and are termed "NPr-MenB PS" herein. Such derivatives and methods for synthesizing the same are described in e.g., U.S. Pat. No. 4,727,136 and EP Publication No. 504,202 B, both to Jennings et al.

The $C_3$–$C_8$ acyl derivatives can be made by first treating native MenB (obtained from e.g., *N. meningitidis* cultures) in the presence of a strong base to quantitatively remove the N-acetyl groups and to provide a reactive amine group in the sialic acid residue parts of the molecule. The deacylated MenB PS fragments are then N-acylated. For example, in the case of NPr-MenB PS, the deacylated molecule is N-propionylated using a source of propionyl groups such as propionic anhydride or propionyl chloride, as described in U.S. Pat. No. 4,727,136 to Jennings et al. The extent of N-acylation can be determined using, for example, NMR spectroscopy. In general, reaction conditions are selected such that the extent of N-acylation is at least about 80%.

In order to increase the immunogenicity of the MenB PS derivatives, the derivatives can be conjugated to a suitable carrier molecule to provide glycoconjugates. Particularly, N-acylated MenB PS glycoconjugate preparations having well defined and controlled structural configurations can be formed from intermediate sized N-acylated MenB oligosaccharides as described below.

Thus, a group of N-acylated MenB PS glycoconjugates, an example of which is termed "COMJ-2" herein can be prepared as follows. An N-acylated MenB PS preparation, having substantially 100% N-acylated MenB sialic acid residues, as determined by e.g., NMR analysis, can be fragmented under mild acidic conditions to provide a population of oligosaccharide molecules of varying sizes. The fragmented products are size fractionated using for example standard ion exchange chromatographic techniques combined with e.g., stepwise salt gradients, to provide fractions of N-acylated MenB molecules of homogenous sizes. Fractions containing intermediate sized oligosaccharides e.g., with an average Dp or about 5 to about 22, preferably 10 to about 20, and more particularly about 12 to about 18, are chemically end-activated at the non reducing termini and conjugated to protein carriers by a reductive amination technique to provide the CONJ-2 glyoconjugation. Successful conjugation can be determined by, e.g., gel filtration, and the final saccharide to protein ratio (w/w) assessed by colorimetric assay.

Glycoconjugates formed from MenB PS derivatives, such as the CONJ-2 are then used herein to elicit the formation of anti-saccharide antibodies in an immunized host a subset of such antibodies should bind to MenB bacteria should not cross-react, or be minimally cross-reactive with host tissue sialic acid residues as determined the binding assays described herein. The antibodies can be fully characterized with respect to isotype the antigenic specificity, functional activity and cross reactivity with host tissue.

For example, mammalian subjects, conveniently standard laboratory animals such as rodents and rabbits, can be summarized with compositions containing the glycoconjugates along with a suitable adjuvant to elicit the production of polyclonal sera. Groups of animals are generally immunized and boosted several times with the compositions. Antisera from immunized animals can be obtained, and polyclonal sera that does not cross-react with host tissue can be obtained using in-situ absorption or conventional affinity chromatography techniques. Successful glycoconjugate antigens can be identified by their ability to elicit a substantial IgG anti MenB PS derivative antibody response, characteristic of a T-cell dependent antigen. Conjugates that are found to be highly immunogenic and produce predominantly IgG antibodies are particularly preferred for use in the methods of the present invention.

MenB PS derivatives that are capable of eliciting the formation of bactericidal antisera are suitable for use in the production of monoclonal antibodies. More particularly, the process used to provide the various MenB PS derivative conjugates is designed to produce superior immunogens presenting unique saccharide-associated epitopes that mimic those found on the surface of MenB organisms and are expressed minimally in the host. The MenB PS derivatives described herein and thus capable of eliciting the production of MenB-specific antibodies which can be use directly in the selective or therapeutic pharmaceutical preparation or, preferably, used to search for mimetics of MenB polysaccharide antigens that will provide unique epitopes for anti-MenB vaccines.

Thus is one embodiment of the invention, selected MenB derivatives are used to provide monoclonal antibodies and functional equivalents thereof. The term "functional equivalent" with respect to a particular that: (a) cross-blocks an exemplified monoclonal antibodies kinds selectively to the MenB PS derivative or glycoconjugate in question; (c) does not cross-react, or minimally cross-reacts, with host PSA as determined using the binding assays described herein; and, optionally, activity (e.g., complement-mediated bactericidal and/or opsonic activity) against MenB bacterial cells as determined by standard assays described below. Further, as used herein with regard to a particular monoclonal antibody producing hybridoma of the invention, the term "progeny" is intended to include all derivatives, issue, and offspring of the parent hybridoma that produce the monoclonal antibody produced by the parent, regardless of generation or karyotypic identity.

Monoclonal antibodies are prepared using standard techniques, well known in the art, such as by the method of Kohler and Milstein, *Nature (*1975) 256:495, or a modification thereof, such as described by Buck et al. (1982) *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

More particularly, somatic cell hybrids can be prepared by the method of Buck et al., (supra), using the azaguanine resistant, non-secreting murine myeloma cell line P3X63-Ag8.653 (obtainable from the ATCC). The hybridoma cell lines are generally cloned by limiting dilution, and assayed for the production of antibodies which bind specifically to the immunizing antigen and which do not bind to unrelated antigens. The selected monoclonal antibody-secreting hybridomas are then cultured either in vitro (e.g., in tissue culture bottles or hollow fiber reactors), or in vivo (e.g., as ascites in mice).

Hybridoma supernatant can be assayed for anti-MenB PS derivative reactive antibody using, for example, either solid phase ELISA or an indirect immunofluorescence assay with the immunizing MenB PS derivative or with native MenB PS (NAc-MenB PS). The selectivity of monoclonal antibodies secreted by the hybridomas can be assessed using competitive specific binding assays, such as inhibition ELISA, or the like. For example, antibody molecules, either diluted in buffer, or buffer containing soluble MenB PS derivatives or NAc-MenB PS, are reacted in an ELISA vessel in the presence of bound MenB PS derivatives. After washing, bound antibody is detected by labeled anti-Ig (anti-IgM, IgG and IgA) as the secondary antibody. Antibodies that are inhibited by the soluble MenB PS derivatives can be considered specific and, thus are selected for further study including, isotyping and additional screening for cross-reactivity, functional activity, and autoreactivity.

Specifically, partially purified monoclonal antibody molecules can be individually evaluated for their ability to bind to host cells which express polysialic acid residues on their cell surfaces. Such cells represent surrogate targets for the detection of antibodies that exhibit autoimmune activity. One target comprises the human neuroblastoma cell line, CHP-134, which expresses long chain α2–8 polysialic acid (NCAM) on its cell surface, as described by Livingston et al. (1988) *J. Biol. Chem.* 263:9443. Other suitable targets include, but are not limited to, newborn brain cells, tissues derived from e.g., kidney, heart and the olfactory nerve, cultured saphenous vein endothelial cells, cytotoxic T lymphocytes and natural killer (NK) cells. See, e.g., Brandon et al. (1993) *Intl. J. Immunopathology and Pharmacology* 6:77. Monoclonal antibody molecules obtained from the hybridomas can be added to suitable test cell populations in culture, and the potential binding of the monoclonals to the cellular targets detected and quantified directly using labeled monoclonals, or indirectly using an appropriately labeled secondary reagent that reacts specifically with each monoclonal antibody (e.g., Staphylococcal Protein A and G and anti-murine antibody molecules). Antibodies that do not cross-react with test host tissue PSA or that display minimal reactivity are not considered autoreactive for purposes of the present invention. Thus, these antibodies are appropriate for further use. In addition, some antibodies that show binding with test tissue, which binding is not affected by pre-treatment of the test cells with neuraminidase, may also be appropriate for further use. Autoreactivity of such antibodies is termed "indeterminate" herein.

Functional activity can be determined by assessing complement-mediated bactericidal activity and/or opsonic activity. In particular, complement-mediated bactericidal activity of the antibodies can be evaluated using standard assays such as those described by Gold et al. (1970) *Infect. Immun.* 1:479, Westerink et al. (1988) *Infect. Immun.* 56:1120, Mandrell et al. (1995) *J. Infect. Dis.* 172:1279, and Granoff et al. (1995) *Clin. Diagn. Laboratory Immunol,* 2:57. In these assays, *N. meningitidis* is reacted with a complement source as well as with the antibody to be tested. Bacterial counts are done at various sampling times. Those antibodies that demonstrate complement-mediated bactericidal activity, as demonstrated by a minimum of a 50% reduction in viable bacterial cell counts determined after sixty minutes incubation with antibody and complement, as compared to colony counts at time zero, are considered to exhibit bactericidal activity for purposes of the present invention and are suitable for further use.

Complement-mediated bacteriolysis is thought to be the major mechanism responsible for host protection against invasive *Meningococcal* disease. However, evidence also supports an important protective role for opsonization (see, e.g., Bjerknes et al. (1995) *Infect. Immun.* 63:160). Accordingly, the opsonic activity of the antibodies produced herein can be evaluated as a second measure, or as an alternative measure, to assess functional activity. Results from opsonic assays can be used to supplement bactericidal data, and to help in the selection of antibodies capable of conferring protection. Evaluation of optimal activity is also particularly useful herein for the evaluation of the murine monoclonal antibodies of the invention which have an IgG1 isotype. Murine IgG1 (in contrast to human IgG1) is ineffective in activation of complement. Thus, murine IgG1 antibodies do not activate complement-mediated bacteriolysis of MenB in the above described assays. However, functional activity of IgG1 anti-NPr-MenB PS monoclonal antibodies can be accessed by opsonization in the absence of complement.

A variety of opsonic assay methods are known in the art and can be used to evaluate functional activity of the monoclonal antibodies of the present invention. Such standard assays include those described by Sjursen et al. (1987) *Acta Path. Microbiol. Immunol. Scand., Sec. C* 95:283, Halstensen et al. (1989) *Scand. J. Infect. Dis.* 21:267, Lehmann et al. (1991) *APMIS* 99:769, Halstensen et al. (1991) *NIPH Annals* 14:157, Fredlund et al. (1992) *APMIS* 100:449, Guttormsen et al. (1992) *Infect. Immun.* 60:2777, Guttormsen et al. (1993) *J. Infec. Dis.* 167:1314, Bjerknes et al. (1995) *Infect. Immun.* 63:160, Hayrinen et al. (1995) *J. Infect. Dis.* 171:1481, de Velasco et al. (1995) *J. Infect. Dis.* 172:262, and Verheul, A. F. M. (1991) "Meningococcal LPS Derived Oligosaccharide-Protein Conjugate Vaccines, Immunochemical and Immunological Aspects," Thesis, Utrecht University, The Netherlands, pp. 112–135.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification.

It may be desirable to provide chimeric antibodies, especially if the antibodies are to be used in preventive or therapeutic pharmaceutical preparations, such as for providing passive protection against MenB., as well as in MenB diagnostic preparations. Chimeric antibodies composed of human and non-human amino acid sequences may be formed from the mouse monoclonal antibody molecules to reduce their immunogenicity in humans (Winter et al. (1991) *Nature* 349:293; Lobuglio et al. (1989) *Proc. Nat. Acad. Sci. USA* 86:4220; Shaw et al. (1987) *J Immunol.* 138:4534; and Brown et al. (1987) *Cancer Res.* 47:3577; Riechmann et al. (1988) *Nature* 332:323; Verhoeyen et al. (1988) *Science* 239:1534; and Jones et al. (1986) *Nature* 321:522; EP Publication No. 519,596, published 23 Dec. 1992, and U.K. Patent Publication No. GB 2,276,169, published 23 Sep. 1994).

Antibody molecule fragments, e.g., F(ab')$_2$, Fv, and sFv molecules, that are capable of exhibiting immunological binding properties of the parent monoclonal antibody molecule can be produced using known techniques. Inbar at al. (1973) *Proc. Nat. Acad. Sci. USA* 69:2659; Hochman et al. (1975) *Biochem* 15:2706; Ehrlich et al. (1980) *Biochem* 19:4091; Huston et al. (1986) *Proc. Nat. Acad. Sci. USA* 85:(16):5879; and U.S. Pat. Nos. 5,091,513 and 5,132,405, to Huston et al.; and U.S. Pat. No. 4,946,778, to Ladner et al.

In the alternative, a phage-display system can be used to expand the monoclonal antibody molecule populations in vitro. Salkl, et al. (1986) *Nature* 324:163; Scharf et al. (1985) *Science* 133:1076; U.S. Pat. Nos. 4,683,195 and 4,683,202; Yang et al. (1995) *J Mol Biol* 254:392; Barbus, III et al. (1995) *Methods: Comp. Meth Enzymol* 8:94; Barbas, III et al. (1991) *Proc Natl Acad Sci USA* 88:7978.

Once generated, the phage-display library can be used to improve the immunological binding affinity of the Fab molecules using known techniques. See, e.g., Fagina et al. (1994) *J. Mol. Biol.* 239:68.

The ongoing sequences for the heavy and light chain portions of the Fab molecules selected from the image display library can be isolated or synthesized, and cloned into any suitable vector or replicon for expression. Any suitable expression system can be used, including for example, bacterial, yeast, insect, amphibian and mammalian systems. Expression systems in bacteria include those described in Chang et al. (1978) *Nature* 275:615, Goeddel et al. (1979) *Nature* 281:544, Goeddel et al. (1980) *Nucleic Acids Res.* 8:4057, European Application No. EP 36,776, U.S. Pat. No. 4,551,433, deBoer et al. (1983) *Proc. Natl. Acad. Sci. USA* 80:21–25, and Siebenlist et al. (1980) *Cell* 20:269.

Expression systems in yeast include those described in Hinnen et al. (1978) *Proc. Natl. Acad. Sci. USA* 75:1929, Ito et al. (1983) *J. Bacteriol.* 153:163, Kurtz et al. (1986) *Mol. Cell. Biol.* 6:142, Kunze et al. (1985) *J. Basic Microbiol.* 25:141, Gleeson et al. (1986) *J. Gen. Microbiol.* 132:3459, Roggenkamp et al. (1986) *Mol. Gen. Genet.* 202:302, Das et al. (1984) *J. Bacteriol.* 158:1165, De Louvencourt et al. (1983) *J. Bacteriol.* 154:737, Van den Berg et al. (1990) *Bio/Technology* 8:135, Kunze et al. (1985) *J. Basic Microbiol.* 25:141, Cregg et al. (1985) *Mol. Cell. Biol.* 5:3376, U.S. Pat. Nos. 4,837,148 and 4,929,555, Beach et al. (1981)

Nature 300:706, Davidow et al. (1985) Curr. Genet. 10:380, Gaillardin et al. (1985) Curr. Genet. 10:49, Ballance et al. (1983) Biochem. Biophys. Res. Commun. 112:284–289, Tilburn et al. (1983) Gene 26:205–221, Yelton et al. (1984) Proc. Natl. Acad. Sci. USA 81:1470–1474, Kelly et al. (1985) EMBO J. 4:475479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. (1988) J. Gen. Virol. 69:765–776, Miller et al. (1988) Ann. Rev. Microbiol. 42:177, Carbonell et al. (1988) Gene 73:409, Maeda et al. (1985) Nature 315:592–594, Lebacq-Verheyden et al. (1988) Mol. Cell. Biol. 8:3129, Smith et al. (1985) Proc. Natl. Acad. Sci. USA 82:8404, Miyajima et al. (1987) Gene 58:273, and Martin et al. (1988) DNA 7:99. Numerous baculoviral strains and variants and corresponding permissive insect host cells from hosts are described in Luckow et al. (1988) Bio/Technology 6:47–55, Miller et al. (1986) GENERIC ENGINEERING, Setlow, J. K. et al. eds., Vol. 8, Plenum Publishing, pp. 277–279, and Maeda et al. (1985) Nature 315:592–594.

Mammalian expression can be accomplished as described in Dijkema et al. (1985) EMBO J. 4:761, Gorman et al. (1982) Proc. Natl. Acad. Sci. USA 79:6777, Boshart et al. (1985) Cell 41:521, and U.S. Pat. No. 4,399,216. Other features of mammalian expression can be facilitated as described in Ham et al. (1979) Meth. Enz. 58:44, Barnes et al. (1980) Anal. Biochem. 102:255, U.S. Pat. Nos. 4,767, 704, 4,657,866, 4,927,762, 4,560,655 and Reissued U.S. Pat. No. RE 30,985, and in International Publication Nos. WO 90/103430, WO 87/00195.

Any of the above-described antibody molecules can be used herein to provide anti-MenB therapeutic or preventive pharmaceutical agents. Additionally, "humanized" antibody molecules, comprising antigen-binding sites derived from the instant murine monoclonal antibodies, can be produced using the techniques described above.

The anti-MenB antibodies of the present invention, described above, are conveniently used as receptors to screen diverse molecular libraries in order to identify molecular mimetics of unique epitopes from MenB. Methods for identifying mimetics in molecular libraries generally involve the use of one or more of the following procedures: (1) affinity purification with an immobilized target receptor; (2) binding of a soluble receptor to tethered ligands; and (3) testing soluble compounds directly in antigen competition assays or for biological activity. Molecules screened for molecular mimics include but are not limited to small organic compounds, combinatorial libraries of organic compounds, nucleic acids, nucleic acid derivatives, saccharides or oligosaccharides, peptoids, soluble peptides, peptides tethered on a solid phase, peptides displayed on bacterial phage surface proteins, bacterial surface proteins or antibodies, and/or peptides containing non-peptide organic moieties.

For example, libraries of diverse molecular species can be made using combinatorial organic synthesis. See, e.g., Gordon et al. (1994) J. Med. Chem. 37:1335. Examples include but are not limited to oligocarbamates (Cho et al. (1993) Science 261:1303); peptoids such as N-substituted glycine polymers (Simon et al. (1992) Proc. Natl. Acad. Sci. USA 89:9367); and vinylogous polypeptides (Hagihara et al. (1992) J. Am. Chem. Soc. 114:6568).

A variety of approaches, known in the art, can be used to track the building blocks as they are added during synthesis so that the history of individual library members can be determined. These approaches include addressable location on a photolithographic chip (oligocarbamates), a deconvolution strategy in which "hits" are identified through recursive additions of monomers to partially synthesized libraries (peptoids, peptides), and coding combinatorial libraries by the separate synthesis of nucleotides (Nielsen et al. (1993) J. Am. Chem. Soc. 115: 9812) or other organic moieties (Ohlmeyer et al. (1993) Proc. Natl. Acad. Sci. USA 90:10922) ("tags"). The coded tags associated with each library member can then be decoded after a mimetic has been selected. For example, nucleic acid tags can be decoded by DNA sequencing.

Peptoid combinatorial libraries are particularly useful for identifying molecular mimetics of unique MenB epitopes. Peptoids are oligomers of N-substituted glycine (Simon et al. (1992) *Proc. Natl. Acad. Sci. USA* 89:9367) and can be used to generate chemically diverse libraries of novel molecules. The monomers may incorporate t-butyl-based side-chain and 9-fluorenylmethoxy-carbonyl $\alpha$-amine protection. The assembly of monomers into peptoid oligomers can be performed, for example, on a solid phase using the "submonomer method" of Zuckermann et al. (1991) *J. Am. Chem. Soc.* 114:10646. In this method, syntheses are conducted with Rink amide polystyrene resin (Rink et al. (1987) *Tetrahedron Lett.* 28:3787). Resin-bound amines are bromoacetylated by in situ activation of bromoacetic acid with diisopropylcarbodiimide. Subsequently, the resin-bound bromoacetamides are displaced by addition of an amine. The amines may incorporate t-butyl-based protection of additional reactive groups. This two-step cycle is repeated until the desired number of monomers is added. The oligopeptide is then released from the resin by treatment with 95% trifluroacetic acid/5% water. The syntheses are performed, preferably, using a robotic synthesizer. See, e.g., Zuckermann et al. (1992) *Pept. Protein Res.* 40:498. In the alternative, oligomerization of the peptoid monomers may be performed by in situ activation by either benzotriazol-1-yloxytris(pyrrolidino)phosphonium hexafluorphosphate or bromotris(pyrrolidino)phosphonium hexafluorophosphate. In this alternative method, the other steps are identical to conventional peptide synthesis using $\alpha$-(9-fluorenylmethoxycarbonyl) amino acids (see, e.g., Simon et al. (1992), supra).

Once the peptoid libraries are generated, they can be screened by, e.g., adding the monoclonal antibodies of the present invention, along with various pools of the combinatorial peptoids, to wells of microtiter plates coated with MenB PS derivatives or MenB bacteria, either alone or as glycoconjugates. After a period of incubation and a wash to remove unbound antibody, the presence of bound antibody is determined by standard ELISA assays. See, e.g., Harlow & Lane, *Antibodies: A Laboratory Manual* (1988), Cold Spring Harbor Laboratory, Cold Spring Harbor, N.Y., 553. Wells that do not contain bound antibody indicate the presence of peptoid mimetics that bind to the antibody. The particular identities of the peptoid mimetics in the pools are determined by recursively adding back monomer units to partially synthesized members of the libraries. Zuckermann et al. (1994) *J. Med. Chem.* 37:2678.

Peptide libraries can also be used to screen for molecular mimetics of unique epitopes of MenB using the anti-MenB antibodies of the present invention. Such libraries are based on peptides such as, but not limited to, synthetic peptides that are soluble (Houghten (1985) *Proc. Natl. Acad. Sci. USA* 82:5131) or tethered to a solid support (Geysen et al. (1987) *Immunol. Methods* 102:259; U.S. Pat. No. 4,708,871) and peptides expressed biologically as fusion proteins (Scott et al. (1990) *Science* 249:386). For a review of peptide combinatorial libraries, see, e.g., Gallop et al. (1994) *J. Med. Chem.* 37:1233.

For example, random soluble peptides, having known sequences, can be synthesized on solid supports and members of the library separated from each other during the repetitive coupling/deprotection cycles in individual labeled polypropylene bags (Houghten (1985) *Proc. Natl. Acad. Sci. USA* 82:5131). Following synthesis, the peptides are cleaved from the solid support and identified by the label on the polypropylene bag. The synthetic peptide library generated using this method can be screened for binding to an antibody having the desired properties by adsorbing individual peptides to microtiter plate wells and determining antibody binding using standard ELISA assays.

Large, libraries of potential peptide mimetics can also be constructed by concurrent synthesis of overlapping peptides as described in U.S. Pat. No. 4,708,871. to Geyser. The synthetic peptides can be tested for interaction with the antibodies by ELISA while still attached to the support used for synthesis. The solid support is generally a polyethylene or polypropylene rod onto which is graft polymerized a vinyl monomer containing at least one functional group to produce polymeric chains on the carrier. The functional groups which are sequentially reacted with amino acid residues in the appropriate order to build the desired synthetic peptide using conventional methods of solid phase peptide chemistry. For example, peptide sequences can be made by parallel synthesis on polyacrylic acid-grafted polyethylene pins arrayed in microtiter plates, as described in Geyser et al. (1987) *J. Immunol. Methods* 102:259. Such libraries can be screened by, e.g., adding antibody to wells containing the peptide-pins. After washing unbound antibody from the cells, the presence of bound antibody can be detected using an ELISA assay.

Peptide mimetics that interact with the antibodies of the present invention can also be identified using biological expression systems. See, e.g., Christian et al. (1992) *J. Mol. Biol.* 227:711; Devlin et. al. (1990) *Science* 249:404; Cwirla et. al. (1990) *Proc. Acad. Sci. USA* 87:6378; Gallop et al. (1994) *J. Med. Chem* 37:1233. Using such systems, large libraries of peptide sequences can be screened for molecules that bind the antibodies of the present invention. This approach also allows for simple molecular characterization of identified mimetics since DNA encoding the peptides can be readily sequenced. Additionally, rare mimetics can be amplified through several rounds of selection/amplification.

For example, phage-display libraries can be produced by inserting synthetic DNA pieces, encoding random peptide sequences, near the 5'-end of the gene encoding the pIII or pVIII protein of the filamentous bacterial phage m13, fd, or f1 (Parmley et al. (1988) *Gene* 73:305; Smith et al. (1993) *Meth. Enzymol.* 217:228). The phage, phagemid, or plasmid DNA containing the gene and randomized extension is then used to transform a suitable host such as *E. coli* or *E. coli* coinfected with a helper phage. The phage isolated from the culture carry pIII (1–5 copies) or pVIII (~4000 copies) surface proteins having the randomized peptide sequences extending from the amino terminus. Phage can be purified by, e.g., affinity purification by biotinylating the receptor antibodies of the present invention, incubating the phage with the biotinylated receptor and reacting the phage on streptavidin-coated plates. Bound phage are eluted and amplified by infecting a suitable host on agar medium and subjected to further rounds of affinity purification. Phage from later rounds of affinity purification can be cloned and propagated, their DNAs sequenced to determine the amino acid sequences of their expressed peptide and their binding to MenB antibodies assessed by ELISA or by a variety of other screening procedures, well known in the art.

Combinatorial libraries of human Fab antibodies can also be displayed on phage surface proteins to select useful molecular mimetics for use herein. Preparation of such libraries has been described hereinabove. See, e.g., Burton et al. (1994) *Adv. Immunol.* 57:191 for a review of such techniques.

Molecular mimetics of MenB unique epitopes can also be identified using the anti-MenB antibodies of the present invention in those methods described by Cull et al. (1992) *Proc. Natl. Acad. Sci. USA* 89:1865. The Cull technique utilizes the DNA binding protein, LacI, to form a link between peptide and its encoding DNA sequence. In this method, DNA encoding randomized peptides is appended to the 3'-end of the LacI gene present on a plasmid. The plasmid also contains the DNA binding site for LacI, lacO. When Lacd is expressed from the plasmid in a suitable host (e.g. *E. coli*), it binds tightly to lacO. Thus, when the cells are lysed, each copy of LacI that displays a randomized peptide at its carboxyl terminus is associated with the DNA encoding it. Methods for screening, amplifying, and sequencing these “peptides-on-plasmids” libraries are the same as those used in phage display, as described above.

Molecular mimetics can also be identified using the anti-MenB antibodies in in vitro, cell-free systems such as the system described by Mattheakis et al. (1994) *Proc. Natl. Acad. Sci. USA* 91:9022. In this approach, nascent peptides are displayed in polysome complexes and construction of libraries, expression of the peptides, and screening is carried out in a cell-free system. Peptides displayed on polysomes can be screened using, for example, an affinity purification/amplification screening procedure where the MenB-specific antibody/receptor is immobilized, e.g., on a plastic plate.

Molecules used in the libraries above can be manipulated in order to form more stable conformations and thus enhance identification of useful molecular mimetics. For example, cysteine residues can be incorporated in the randomized sequences to form disulfide loops (O’Neal et al. (1992) *Proteins* 14:509) and protein scaffolds can be used to display randomized peptides in internal loop segments (Freimuth et al. (1990) *J. Biol. Chem.* 265:896; Sollazzo et al. (1990) *Prot. Engin.* 4:215).

Anti-idiotypic antibodies can also be produced using the anti-MenB antibodies of the present invention for use as molecular mimetics of unique epitopes of MenB. For a review of anti-idiotype antibodies, see, e.g., Kieber-Emmons et al. (1986) *Int. Rev. Immunol.* 1:1. In this regard, the pocket or cleft formed by the heavy and light chains of an antibody is often intimately involved in antigen binding. This region, called the paratope, is an “internal image” of the antigen surface bound by the antibody. An antibody directed against the paratope is one of several potential anti-idiotypic antibodies and can be a mimetic of the antigen. Randomized peptide loops of the heavy and light chains occur naturally as part of the generation of antibody diversity.

Anti-MenB monoclonal antibodies of the present invention can be used to elicit anti-idiotype antibody production and to select anti-idiotypes bearing the “image” of the antigen, using the techniques described in e.g., Westerink et al. (1988) *Infect. Immun.* 56:1120.

In one embodiment, a combinatorial library of phage-display antibodies, as described above, are screened using the anti-MenB monoclonal antibodies of the present invention to identify mimetic antibodies, i.e. phage-display Fab anti-idiotypic antibodies.

Anti-idiotype antibodies produced can be easily tested for their ability to elicit anti-MenB antibody production in standard laboratory animal models. The variable genes of the anti-idiotype antibodies can be sequenced to identify peptide vaccine candidates.

Additionally, combinatorial libraries of oligonucleotides (DNA, RNA, and modified nucleotides) can be screened to find molecular mimetics that bind to the non-autoreactive, anti-MenB antibodies of the present invention. Techniques for the production and use of such libraries are reviewed in e.g., Gold et al. (1995) *Annu. Rev. Biochem.* 64:763. A system, known as SELEX for Systematic Evolution of Ligands by Exponential enrichment, can be used for rapidly screening vast numbers of oligonucleotides for specific sequences that have desired binding affinities and specificities toward the anti-MenB antibodies. (Tuerk et al. (1990) *Science* 249:505). For example, immobilized non-autoreactive MenB monoclonal antibodies can be used to affinity purify specific binding oligonucleotides from a combinatorial library. The bound oligonucleotides are released from the immobilized antibodies by adding a competitive ligand or lowering the pH. The released oligonucleotides are either amplified directly using the polymerase chain reaction or converted to double stranded DNA using reverse transcriptase (Tuerk et al., 1990, supra). This is followed by additional rounds of selection and amplification until the desired mimetic is obtained. The sequences of the oligonucleotide mimetics are determined by DNA sequencing.

Once putative molecular mimetics are identified, they are tested for their ability to elicit functionally active (e.g., bactericidal and/or opsonic) antibodies which lack autoreactivity or have minimal autoreactivity, as described above. Molecular mimetics that have these properties are appropriate for further use, for example, in vaccine compositions.

The anti-MenB monoclonal antibodies can also be used to investigate the bactericidal and/or opsonic function of antibodies of different specificities, as well as to identify the molecular nature of the unique epitopes on the MenB bacterial surface that are not cross-reactive with host PSA. Furthermore, the anti-MenB antibodies can be used to isolate fractions of MenB bacteria or MenB PS derivatives. Once isolated, the critical epitopes reactive with the anti-MenB antibodies can be characterized and employed directly in oligosaccharide protein conjugate vaccines or to model synthetic saccharides or mimetics for use in vaccines.

Molecular mimetics identified using the functionally active anti-MenB antibodies of the invention can be used to generate antibody reagents for use in diagnostic assays. For example, antibodies reactive with the molecular mimetics can be used to detect bacterial antigen in biological samples using immunodiagnostic techniques such as competition, direct reaction, or sandwich type assays. Such assays include Western blots; agglutination tests; enzyme-labeled and mediated immunoassays, such as ELISAs; biotin/avidin type assays; radioimmunoassays; immunoelectrophoresis; immunoprecipitation, and the like.

In addition, molecular mimetics, unique (e.g., non-autoimmune) Men B epitopes identified using the molecular mimetics and anti-id monoclonal antibodies can be used herein in vaccine compositions for the prevention of MenB disease in vaccinated subjects.

The vaccine compositions can comprise one or more of the anti-id monoclonal antibodies, molecular mimetics or non-autoimmune epitopes of MenB. The vaccines may also be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES.

The vaccines will generally include one or more "pharmaceutically acceptable excipients or vehicles" such as water, saline, glycerol, ethanol, etc. Additionally, auxiliary substances, such as wetting or emulsifying agents of buffering substances, and the like, may be present is any vehicles.

Adjuvants may also be used to enhance the effectiveness of the vaccines; Adjuvants can be added directly to the vaccine compositions or can be administered separately, either concurrently with or shortly after, vaccine administration. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% TWEEN 80 (polyoxyethylene-sorbitan monooleate), and 0.5% SPAN 85 (sorbitan trioleate) (optionally containing various amounts of MTP-PE (see below), although not required) formulated into submicron particles using a microfluidizer such as Model 11Y microfluidizer (Microfluidics, Newton, Mass.), (b) SAF, containing 10% Squalane, 0.4% TWEEN 80 (polyoxyethylenesorbitan monooleate), 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN 80 (polyoxyethylenesorbitan monooleate), and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™(Cambridge Bioscience, Worcester, Mass.) may be used or particle generated therefrom such as ISCOMs (immunostimulating complexes); (4) Freund's Complete Adjuvant (FCA) and Freund's Incomplete Adjuvant (FICA); (5) cytokines, such as interleukins (IL-1, IL-2, etc.), macrophage colony stimulating factor (M-CSF), tumor necrosis factor (TNF), etc.; and (6) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

In order to enhance the effectiveness of vaccine compositions formed from a molecular mimetic, it may be necessary to conjugate the mimetic to a carrier molecule. Such carrier molecules will not themselves induce the production of harmful antibodies. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), inactive virus particles, $CRM_{197}$ (a nontoxic mutant diphtheria toxin), and the like. Such carriers are well known to those of ordinary skill in the art. The mimetic conjugates are selected for their ability to express epitopes that closely resemble those found on the surface of MenB bacterial cells. Suitable conjugates thus elicit the formation of antibodies that have functional activity against bacteria, and do not cross-react, or are minimally cross-reactive with polysialic acid in host tissue as determined using the binding assays described herein.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes, or adsorbed to particles for enhanced adjuvant effect, as discussed above.

The vaccines will comprise an effective amount of the anti-id monoclonal antibody; molecular mimetic, peptide molecular mimetic or complexes of proteins; or nucleotide sequences encoding the same, and any other of the above-mentioned components, as needed. By "an effective amount" is meant an amount of a molecule which will induce an immunological response in the individual to which it is administered and poses a minimal risk of stimulating an autoimmune response in the individual. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδ T cell populations.

Once formulated, the vaccines are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule.

Polynucleotides encoding DNA or RNA mimetics of the MenB PS can also be used in vaccines for nucleic acid immunization. In the alternative, polynucleotides encoding peptide mimetics can be used in nucleic acid immunization. Such methods generally comprise the introduction of a polynucleotide encoding one or more of the desired molecules into a host cell, for the in vivo expression of the nucleic acid molecules or proteins. The polynucleotide can be introduced directly into the recipient subject, such as by injection, inhalation or the like, or can be introduced ex vivo, into cells which have been removed from the host. In the latter case, the transformed cells are reintroduced into the subject where an immune response can be mounted against the molecule encoded by the polynucleotide. Methods of nucleic acid immunization are known in the art and disclosed in e.g., International Publication No. WO 93/14778 (published 5 Aug. 1993); International Publication No. WO 90/11092 (published 4 Oct. 1990); Wang et al. *Proc. Natl. Acad. Sci. USA* (1993) 90:4156; Tang et al. *Nature* (1992) 356:152; and Ulmer et al. *Science* (1993) 259:1745. Generally, the polynucleotide is administered as a vector which has been encapsulated in a liposome and formulated into a vaccine composition as described above.

The anti-MenB monoclonal antibodies of the present invention, and functional equivalents thereof, can be used in pharmaceutical compositions to treat and/or prevent MenB and *E. coli* K1 disease in mammals. Such disease includes bacterial meningitis and sepsis, in infants, children and adults. In this regard, the administration of a highly-active, anti-MenB monoclonal antibody preparation to an individual who is at risk of infection, or who has been recently exposed to the agent will provide immediate passive immunity to the individual. Such passive immunizations would be expected to be successful in both normal and immunocompromised subjects. Further, administration of such monoclonal antibody compositions can be used to provide antibody titer to MenB in a mammalian subject, either alone, or in combination with known anti-MenB therapeutics.

The pharmaceutical compositions of the present invention generally comprise mixtures of one or more of the above described anti-MenB monoclonal antibodies, including Fab molecules, Fv fragments, sFv molecules and combinations thereof. The compositions can be used to prevent MenB disease or to treat individuals following MenB infection.

Therapeutic uses of the pharmaceutical compositions involve both reduction and/or elimination of the MenB infection agent from infected individuals, as well as the reduction and/or elimination of the circulating MenB agent and the possible spread of the disease.

As described above in regard to the vaccine compositions of the present invention, the pharmaceutical compositions can be administered in conjunction with ancillary immunoregulatory agents such as IL-2, modified IL-2 (cyc125→ser125), GM-CSF, IL-12, γ-interferon, IP-10, MIP1β and RANTES.

The preparation of pharmaceutical composition containing one or more antibodies, antibody fragments, sFv molecules or combinations thereof, as the active ingredient is generally known to those of skill in the art. Once formulated, the compositions are conventionally administered parenterally, e.g., by injection (either subcutaneously, intravenously or intramuscularly). Additional formulations suitable for other modes of administration include oral and pulmonary formulations, suppositories, and transdermal applications.

The pharmaceutical compositions are administered to the subject on be treated in a manner compatible with the dosage formulation and in an amount that will be prophylactically and/or therapeutically effective. The amount of the composition to be delivered, generally in the range of from about 50 to about 10,000 micrograms of active agent per dose, depends on the subject to be treated, the capacity of the subject's immune system to mount its own immune-responses, and the degree of protection desired. The exact amount necessary will vary depending on the age and general condition of the individual to be treated, the severity of the condition being treated and the mode of administration, among other factors. An appropriate effective amount can be readily determined by one of skill in the art. Thus, "an effective amount" of the pharmaceutical composition will be sufficient to bring about treatment or prevention of MenB disease symptoms, and will fall in a relatively broad range that can be determined through routine trials.

In addition, the pharmaceutical compositions can be given in a single dose schedule, or preferably in a multiple dose schedule. A multiple dose schedule is one in which a primary course of administration may be with 1–10 separate doses, followed by other doses given at subsequent time intervals needed to maintain or reinforce the action of the compositions. Thus, the dosage regimen will also, at least in part, be determined based on the particular needs of the subject to be treated and will be dependent upon the judgement of the reasonably skilled practitioner.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of "Sized" Glycoconjugates

An exemplary NPr-MenB oligosaccharide-tetanus toxoid conjugate vaccine, hereinafter referred to as CONJ-2, was prepared as follows. The N-acetyl groups of MenB B polysaccharide were removed by heating the polysaccharide to 110° C. in 2M NaOH for 6 hours in the presence of $NaBH_4$. The de-acetylated polysaccharide was exhaustively dialyzed in saturated sodium bicarbonate buffer then stirred with an excess of propionic anhydride for 12 hours at ambient temperature. The solution was exhaustively dialyzed in water and the N-propionylated meningococcal B (NPr-MenB PS) polysaccharide was recovered by lyophilization.

For preparation of the conjugate vaccine, the NPr-MenB polysaccharide was partially hydrolyzed in 10 mM sodium acetate at pH 5.5 at 50EC for 2 hours. The resulting mixture of oligosaccharides was fractionated on Q-SEPHAROSE (a quaternary ammonium strong anion exchanger). Oligosaccharides having an average degree of polymerization (Dp) of 2–6 were first eluted with 100 mM NaCl and discarded. Intermediate-sized oligosaccharides were eluted with 500 mM NaCl. It was subsequently determined by analytical ion exchange chromatography using a MONO Q column (a quaternary ammonium strong anion exchanger) that the intermediate-sized oligosaccharides ranged in size from Dp 13 to 20 (Mean=Dp 13).

A terminal aldehyde group was generated at the non-reducing end of the intermediate-sized oligosaccharides by reacting them with 100 mM sodium periodate for 15–30 minutes at ambient temperature in the dark. Excess ethylene glycol was used to quench the oxidative reaction and the product was desalted on a SEPHADEX G-25 column (a dextran-based column). The oligosaccharide-protein conjugate was prepared by stirring a mixture of terminal aldehyde containing NPr MenB oligosaccharide with tetanus toxoid (molar ratio of 200:1, respectively) in 0.75 M potassium phosphate buffer, pH 9.0 with 40 mg/ml of sodium cyanoborohydride for one day at 40EC and two days at ambient temperature. The resultant NPr-MenB oligosaccharide-tetanus toxoid conjugate (CONJ-2) was finally purified by gel permeation chromatography on SEPHADEX G-100 (a dextran-based matrix) using 50 mM sodium phosphate, pH 7.0, 150 mM sodium chloride as the eluting buffer. Sialic acid and protein compositions of the conjugate vaccine were measured by the Svennerholm resorcinol reaction (Svennerholm, L. (1957) *Biochim. Biophys. Acta.* 24:604) and Lowry assays, respectively. On a weight basis, the final saccharide-to-protein ratio of the CONJ-2 conjugates ranged from 0.10 to 0.25.

EXAMPLE 2

Characterization of the Glycoconjugates

The CONJ-2 glycoconjugate was characterized as follows. In order to demonstrate covalence (e.g., establishing a covalent linkage between the NPr-MenB OS and the protein carrier), a number of physico-chemical techniques can be used, including: SDS-PAGE; Western Blot; SEPHADEX G-100 gel filtration; or the like. For the purposes of the present study, SDS-PAGE was used to establish covalent attachment of the NPR-MenB OS/TT CONJ-2 glycoconjugates by revealing a shift to higher molecular weight for the conjugate band as compared to the carrier protein band, per Se. Western blot analysis of the CONJ-2 glycoconjugates demonstrated covalence by the coincidence of positive immunoreactive signals for TT and NPr-MenB PS with specific anti-TT and anti-NPr-MenB PS antisera.

Based on steric factors, the use of oligosaccharides instead of large molecular weight polysaccharides in the preparation of the CONJ-2 glycoconjugates allows for higher coupling efficiency of saccharide antigens onto the protein carrier molecule. The final saccharide-to-protein ratio of these NPr-MenB oligosaccharide-based conjugates range from about 0.10 to 0.25 which corresponds to about 3 to 5 NPr-MenB oligosaccharide chains covalently bound per protein carrier. On a per weight basis, the CONJ-2 glycoconjugates appear to have a higher saccharide loading than a previously reported NPr-MenB polysaccharide-based conjugate (U.S. Pat. No. 4,727,136) wherein CONJ-2 contains, on the average, about 7.5 to 18.8 times more saccharide (using 10,000 Daltons as the molecular weight of NPr-MenB PS).

In addition, constructing the CONJ-2 glycoconjugates to have substantially homogenous-sized saccharide moieties of a well-defined intermediate chain length (e.g., average Dp of 10–20) is expected to result in glycoconjugates which display more consistent immunological behavior. Further, the selective end-activation (e.g., selective introduction of the aldehyde group at the non-reducing terminus) of the Q-SEPHAROSE chromatography-purified NPr-MenB oligosaccharides avoids the possibility of cross-linked, heterogenous structures which could arise from the use of NPr-MenB PS molecules with "active" aldehyde groups introduced at both termini. In this regard, it is likely that bi-terminally activated PS (having aldehyde groups at both ends) could be derived from a periodate oxidation of N-acylated MenB PS previously exposed to $NaBH_4$ during the N-deacetylation procedure.

EXAMPLE 3

Preparation of Monoclonal Antibodies 4 to 6 week old female CD1 mice were vaccinated by ip injection using a composition containing an NPr-MenB OS/TT (CONJ-2) glycoconjugate antigen and (except for the last booster injection) FCA. Vaccinations were administered at one month intervals for a total of 2 or 3 dosages (including the booster immunization). Three days prior to fusion, the primed animals were boosted with the NPr-MenB OS/TT (CONJ-2) glycoconjugate antigen in the absence of adjuvant. The final volume of each dose was 0.1 ml, which contained 2.5 µg of sialic acid. After the booster injection, the animals were splenectomized and the spleen cells were prepared for fusion with myeloma cells.

Approximately one week before fusion, non-secreting murine P3X63-Ag8.653 myeloma cells (available from the ATCC under accession number ATCC-1580-CRL), were expanded in complete RPMI-1640 medium with 25 mM HEPES buffer and L-Glutamine (GIBCO BRL 041-02400). The cell cultures were assessed periodically to monitor cell growth, cell numbers and to screen for contamination.

On the day of fusion, the spleen cells and the partner P3X63-Ag8.653 myeloma cells (AgS cells) were washed, harvested and mixed at a ratio of 5:1 (spleen cells:myeloma cells). The cell fusions were performed at 37° C. in the presence of 50% polyethylene glycol (PEG). The resulting cell pellets were harvested and plated into 96 well flat-bottom cell culture plates (COSTAR 3596) and incubated under suitable conditions (e.g., at 37° C. in 5% $CO_2$). After one day of incubation, selective medium containing hypoxanthine, aminopterin and thymidine (HAT) was added to each well.

Hybridomas from wells containing growing cells and exhibiting about 10 to 25% confluence were selected for screening after about two weeks of incubation in the HAT selective medium. Selected hybridoma supernatants were screened using a solid phase avidin-biotinylated NPr-MenB PS based ELISA assay. Specificity of antibody binding in the supernatants was determined using soluble NPr-MenB PS as the inhibitor. Negative controls included RPMI medium, Ag8 myeloma supernatant and irrelevant monoclonal antibody preparations. Pooled polyclonal sera from mice immunized with the NPr-MenB OS/TT (CONJ-2) glycoconjugate was used as the positive control. After overnight incubation with the supernatants, the reaction wells were washed and bound immunoglobulin was detected with alkaline phosphatase-labelled polyvalent anti-murine immunoglobulins (IgG, IgA, IgM).

Candidate hybridomas were identified based on their demonstrated binding affinity for NPr-MenB PS in the above-described ELISA assay. Hybridomas secreting highly reactive antibody molecules were cloned by limiting dilution. Particularly, candidate hybridoma cell lines were plated at 0.3, 1.0 and 3.0 cell/well in Terasaki plates (NUNC) in 20 µl of cloning/expansion medium (Complete RPMI-1640 with IL6). After two weeks, the cultures were visually inspected for growth. Frequency analysis was performed using the least squares method described by Lefkovits et al. (1984) *Immun. Today* 5(9):265. The ELISA assay used to identify reactive supernatant among the master wells was repeated to assess antibody activity on days 7 and 14. Selected clones were then expanded and frozen for subsequent use in tissue culture and ascites production. A panel of 39 hybridomas was thus produced, and the secreted monoclonal antibody molecules obtained therefrom (termed "SEAM monoclonal antibodies," particularly, monoclonal antibodies SEAM-1 through SEAM-24, SEAM-26, SEAM-28 through SEAM-31, SEAM-33 through SEAM-36, SEAM-38 through SEAM-42, and SEAM-48) were prepared for further evaluation.

More particularly, selected monoclonal antibodies were produced either in tissue culture, or in ascitic fluid using Pristane-primed 7 to 8 week old male Balb/c mice. Each animal subject was primed by i.p. injection with 0.5 ml Pristane one week prior to inoculation with hybridoma cells. Prior to inoculation, the hybridoma cell concentrations were adjusted to between $2.5 \times 10^6$ and $3 \times 10^6$ cells/ml using sterile PBS. The primed animals were injected i.p. with 1 ml of hybridoma cells, wherein each clonal cell line was inoculated into three different mice. One to two weeks after inoculation, ascites fluid collection was started and continued for a period of approximately one week. The collected fluid was centrifuged at ambient temperature for 10 minutes at 2700 rpm (1500×g). Supernatants were harvested and pellets discarded. The isolated ascites fluid was stored at 4° C. over the course of collection, and fluid collected on different days was pooled, aliquoted and frozen at −70° C.

EXAMPLE 4

Characterization of the Monoclonal Antibodies

The concentrations of unpurified monoclonal antibodies were determined using an ELISA capture assay and a radial immunodiffusion assay. Particularly, a capture ELISA procedure was used to determine the concentration of each of the anti-NPr-MenB PS monoclonal antibodies. Microtiter plates (IMMULON 2, available from Dynatech Laboratories, Inc.) containing 100 µg/well of affinity purified rabbit anti-murine IgG, IgM and IgA (H and L, Zymed) diluted to 1 µg/ml in 10 mM PBS (pH 7.4) were incubated overnight at 4EC. After washing three times with PBS, the wells were filled with 250 µl of Blocking Buffer (PBS containing 1% bovine serum albumin (BSA) and 0.1% sodium azide, pH 7.4) and incubated for 30 to 60 minutes at ambient temperature to block nonspecific binding sites. The plates were washed three times with Washing Buffer (PBS containing 0.1% TWEEN 20 (polyoxyethylenesorbitan monolaurate) and 0.1% sodium azide, pH 7.4). Antibodies to be tested were diluted in Diluting Buffer (PBS containing 1% BSA, 0.1% TWEEN 20 (polyoxyethylenesorbitan monolaurate) and 0.1% sodium azide, pH 7.4) and then added at 100 µl per each well. The plates were covered and incubated overnight at 4EC. Murine IgG1, IgG2b, IgG3 and IgM immunoglobulin standards (available from Southern Biotechnology Associates), at concentrations ranging from 500 ng/ml to 4 ng/ml, were used to construct standard curves for quantifying antibody concentrations.

After incubation overnight, the wells were washed five times with cold Washing Buffer and incubated for 3 hours at 4° C. with 100 µl/well of alkaline phosphatase conjugated anti-murine IgG, IgM and IgA polyclonal antibodies (H and L, Zymed) that were diluted 1:2000 in Diluting Buffer. The plates were then washed with cold Washing Buffer, and 100 µl of freshly prepared substrate (p-Nitrophenyl phosphate, Sigma) diluted to 1 mg/ml in Substrate Buffer (1.0 M diethanolamine, 0.5 mM $MgCl_2$, pH 9.8) was added to each well. Absorbance values at 405 nm were measured after approximately 30 minutes. Immunoglobulin concentrations of the monoclonal antibody preparations were calculated from the standard curves.

Radial immunodiffusion assays were conducted as follows. Radial immunodiffusion plates and reagents were obtained from The Binding Site Limited (Birmingham, England). The assay protocol was then based on the manufacturer's specific instructions supplied with the RID kit. Briefly, calibrator antibody supplied with the kit was reconstituted with an appropriate amount of distilled water. 1:2 and 1:10 dilutions of calibrator antibody were prepared. Test samples can be diluted in 1% BSA if necessary. Aliquots of 10 µl (20 µl for IgA and IgG2a subclass antibodies) for calibrator antibody (neat, 1:2, and 1:10 dilutions) and test samples were applied to separate wells on the plate and incubated for 120 hours at room temperature. The concentrations of the antibodies were determined by measuring the precipitation ring diameters and comparing these values to a reference table included with the RID kit.

The monoclonal antibodies from tissue culture or ascitic fluid were then partially purified as follows. Tissue culture supernatant or ascites containing the monoclonals (200 ml or indicated volume) was added slowly to an equal volume of cold 100% saturated ammonium sulfate (SIGMA, Saint Louis, Mo.) while stirring the solution gently. The monoclonal antibody and Ammonium sulfate mixture was incubated overnight at 4° C. The following morning, the mixture was stirred gently to homogeneity and centrifuged at 5000 rpm in a Sorvall SS34 rotor for 30 minutes at 4° C. After decanting the supernatant, an equal volume of 50% ammonium sulfate solution (i.e. same volume as the 100% saturated ammonium sulfate) was used to wash and resuspend the pellet. The resulting mixture was centrifuged at 5000 rpm in a Sorvall SS34 rotor for 30 minutes at 4° C. The supernatant was then decanted and drained.

For ascites, the pellet was reconstituted in 0.3–0.5 volumes of the starting volume in PBS Buffer (50 mM sodium phosphate, 150 mM sodium chloride, pH 7.4).

For tissue culture supernatant, the pellet was reconstituted in 0.1 volumes of the starting volume of PBS Buffer. The reconstituted monoclonal antibody and ammonium sulfate mixture was placed in a dialysis tubing (molecular weight cut off 10,000–12,000) and allowed to dialyze in 4 L of PBS overnight. The PBS solution was changed 3 to 4 times over the following two days. Monoclonal antibody molecules from the dialysis tubes were transferred into a syringe and sterile filtered through a 0.2 μm membrane filter, and then stored at −20° C.

The partially purified monoclonal antibody preparations were then characterized for (a) immunoglobulin isotype, (b) concentration-dependent binding to NPr-MenB PS, (c) the ability of various NPr-MenB oligomers to inhibit binding to NPr-MenB PS, (d) cross-reactivity with native MenB PS, (e) cross-reactivity with virulent strains of MenB, (f) complement-mediated bactericidal activity, (g) opsonic activity, and (h) autoreactivity as demonstrated by binding to a neuroblastoma cell line that expresses long chain α2–8 linked polysialic acid at the cell surface. In these experiments, the concentrations of monoclonal antibody were measured by the capture ELISA and RID assay described above.

(a) Isotyping of the Antibodies:

The isotypes of the monoclonal antibodies (heavy and light chains) were determined by ELISA using the above-described protocol for the anti-NPr-MenB PS ELISA with the only difference that the secondary alkaline phosphatase-conjugated antibody was specific for IgG subclasses, IgM, IgA and κ and λ light chains. A kit was also used to isotype the antibody molecules. The kit consisted of typing stick substrates coated with goat antibodies specific for the different types of immunoglobulin peptide chains. The kit provides a peroxidase-labelled species specific for anti-murine immunoglobulin to detect the murine monoclonal antibodies bound to the goat antibodies on the substrate.

As depicted below in Table 1, the isotypic distribution among the 39 monoclonal antibodies was found to consist of one IgM and thirty-eight IgG (eight IgG1, five IgG2a, sixteen IgG2b, and nine IgG3). In addition, all antibody molecules had K light chains.

TABLE 1*

| Fine Antigenic Specificity Group (a) | SEAM Monoclonal Antibody Number | Ig Isotype | ELISA Reactivity to N-Pr-MenB PS (b) | ELISA Inhibition of N-Pr-MenB Binding by N-Pr-MenB OS (c) | ELISA Reactivity to N-Ac-MenB PS (d) | Binding to Encapsulated *Neisseria meningitidis* group B (e) | Binding to CHP134 PSA (f) | Bactericidal Activity (g) | Opsono-phagocytotic Activity (g) |
|---|---|---|---|---|---|---|---|---|---|
| I | 10 | G1, κ | + + + | + + + | + + | + | 0 | ND | 0 |
|   | 11 | G2b, κ | + + + | + + | + + + | + | + + | + + | ND |
|   | 18 | G2b, κ | + + + | + + + | + + + | + | + | + + + | + + |
|   | 20 | G2b, κ | +/− | + + | + + | 0 | 0 | 0 | ND |
|   | 21 | G2b, κ | +/− | + + + | + + | 0 | 0 | 0 | ND |
|   | 26 | G2b, κ | + + + + | + | + + + | + | + + | + + | ND |
|   | 28 | G2b, κ | + + + + | + + | + + | + | + | + + | + + |
|   | 29 | G2a, κ | + + + + | + + | + + | + | + + | 0 | ND |
|   | 35 | G2b, κ | + + + + | + | + + + | + | + + | + + + | + + |
| II | 12 | G2a, κ | + + + + | 0 | + + | + | + | + + + | + + |
|   | 13 | G3, κ | + + + | 0 | + + + | + | + + | + + + | + + + + |
|   | 14 | G2b, κ | + + + + | 0 | + + + | + | + + | + + | ND |
|   | 15 | G2b, κ | + + + + | 0 | + + + | + | + + | + + | ND |
|   | 16 | G2b, κ | + + + | 0 | + | + | i | + + | 0 |
|   | 30 | G3, κ | + + + | 0 | + + + | + | + + | + + + | + + + + |
| III | 1 | G3, κ | + | + | 0 | 0 | 0 | + + | ND |
|   | 3 | G2b, κ | + + + + | + + + | 0 | + | 0 | + + | + + + + |
|   | 4 | G1, κ | + + | + + | 0 | i | i | ND | ND |
|   | 5 | G3, κ | +/− | + | 0 | + | 0 | + + + | 0 |
|   | 7 | G3, κ | + | + | 0 | i | i | + + + | 0 |
|   | 8 | G3, κ | + + + | + + + | 0 | + | 0 | + + + | 0 |
|   | 17 | M, κ | + | + + + | 0 | 0 | 0 | 0 | ND |
|   | 19 | G2a, κ | + + | + + | 0 | 0 | i | 0 | ND |
|   | 22 | G2b, κ | + | + + | 0 | 0 | i | 0 | ND |
|   | 23 | G2b, κ | + + | + | 0 | 0 | 0 | 0 | ND |
|   | 48 | G2b, κ | + + + | + + + | 0 | + | 0 | + + | + + |
| IV | 2 | G3, κ | +/− | 0 | 0 | 0 | 0 | + + + | 0 |
|   | 6 | G3, κ | +/− | 0 | 0 | 0 | i | 0 | ND |
|   | 9 | G1, κ | + + | 0 | 0 | 0 | i | ND | ND |
|   | 24 | G2b, κ | + + | 0 | 0 | + | 0 | 0 | ND |
| ND | 31 | G1, κ | +/− | ND | + | + | i | ND | ND |
|   | 36 | G2a, κ | + + + | ND | + + | + | + + | + + | ND |
|   | 39 | G2a, κ | +/− | ND | + + | 0 | + + | 0 | ND |
|   | 40 | G1, κ | + + + + | ND | + | + | + + | 0 | ND |
|   | 41 | G2b, κ | + + | ND | + | + | 0 | + + | 0 |
|   | 33 | G1, κ | + | ND | 0 | 0 | 0 | ND | ND |
|   | 34 | G3, κ | +/− | ND | 0 | 0 | 0 | 0 | ND |

TABLE 1*-continued

| Fine Antigenic Specificity Group (a) | SEAM Monoclonal Antibody Number | Ig Isotype | ELISA Reactivity to N-Pr-MenB PS (b) | ELISA Inhibition of N-Pr-MenB Binding by N-Pr-MenB OS (c) | ELISA Reactivity to N-Ac-MenB PS (d) | Binding to Encapsulated *Neisseria meningitidis* group B (e) | Binding to CHP134 PSA (f) | Bactericidal Activity (g) | Opsonophagocytotic Activity (g) |
|---|---|---|---|---|---|---|---|---|---|
| | 38 | G1, κ | +/− | ND | 0 | 0 | 0 | ND | ND |
| | 42 | G1, κ | +/− | ND | 0 | + | i | ND | ND |

*The data reported in Table 1 represent the results of repeated studies as described herein, and are subject to some variance due to use of different antigen sources in the ELISA procedure, and different complement sources in the bactericidal assay.
(a) Defined by cross-reactivity with N-Ac-MenB PS by ELISA and inhibition of anti-N-Pr-MenB PS binding by short N-Pr-MenB oligomers.
(b) Concentration of monoclonal antibody required to yield an OD of 0.5: +/−, 5–25 μg/ml; +, 1.0–4.9 μg/ml; + +, 0.1–0.9 μg/ml; + + +, 0.01–0.09 μg/ml; + + + +, <0.01 μg/ml.
(c) 0, <25% inhibition; +, 26–48% inhibition; + +, 49–74% inhibition; + + +, 75–100% inhibition when tested at OD 0.5 to 1; Dp 3.8 N-Pr-MenB fragments.
(d) 0, OD < 0.15; +, OD 0.15–0.5; + +, OD 0.5–1.0; + + +, OD > 1.0 when tested at 5 to 25 μg/ml of antibody by ELISA.
(e) 0, no detectable binding to encapsulated strains when tested at 100 μg/ml; +, binding to encapsulated strains 8047 and NmB, but not to non-encapsulated strain M7; i, indeterminate (see text).
(f) 0, no binding activity to polysialic acid (PSA) when tested at 100 μg/ml of antibody; + +, binding activity when tested at 10 μg/ml and inhibitable by neuraminidase treatment; +, binding activity detected at 100 but not 10 μg/ml; i, indeterminate is binding activity not inhibitable by neuraminidase treatment.
(g) + + + +, activity with both rabbit and human complement, and in the absence of complement; + + +, activity with both rabbit and human complement; + +, activity with rabbit complement, no activity with human complement; 0, no activity with rabbit complement or human complement (also includes antibodies only tested with rabbit complement); ND, not done.

(b) Concentration-Dependent Binding to NPr-MenB PS:

A solid phase ELISA procedure was used to assess the concentration dependent binding of the antibody molecules to NPr-MenB PS in the presence of buffer alone or 25 μg/ml of a soluble NPr-MenB PS inhibitor. Biotinylated NlPr-MenB PS-ADH was prepared using the method of Sutton et al. (1985) *J. Immunol. Methods* 82:215. Microtiter plates (IMMULON 2, available from Dynatech Laboratories, Inc.) containing 100 μl/well of avidin (4 μg/ml Extr Avidin, Sigma) in 10 mM PBS (pH 7.4) were incubated overnight at 4EC. After washing three times with PBS, 100 μl of biotinylated NPr-MenB PS in PBS was added to each well and incubated at 37EC for 2 hours. The plates were washed three times with PBS, and the wells were filled with 250 μl of Blocking Buffer and incubated for 30 to 60 minutes at ambient temperature to block nonspecific binding sites.

After blocking, the plates were washed three times with Washing Buffer. 50 μl aliquots of various dilutions of the monoclonals were added to wells of replicate plates containing either 50 μl of Diluting Buffer or 50 μl of Diluting Buffer containing 50 μg of soluble NPr-MenB PS per ml (for a final inhibitor concentration of 25 μg/ml). The plates were then covered and incubated overnight at 4° C. On the following day, the wells were washed five times with cold Washing Buffer and then incubated for 3 hours at 4° C. with 100 μl/well of alkaline phosphatase conjugated anti-murine IgG, IgM and IgA polyclonal antibodies (Zymed) diluted 1:2000 in Diluting Buffer. The plates were then washed with cold Washing Buffer, and 100 μl of freshly prepared substrate (p-Nitrophenyl phosphate, Sigma) diluted to 1 mg/ml in Substrate Buffer was added to each well. Absorbance values at 405 nm were measured after approximately 30 minutes.

FIGS. 1A–1D show the dose-response binding activity of four representative anti-NPr-MenB PS monoclonal antibodies (SEAM-3, SEAM-5, SEAM-16 and SEAM-18, respectively), to solid phase NPr-MenB PS as determined by ELISA. Data shown are for the antibodies diluted in buffer (●), or in buffer containing 25μg/ml of soluble NPr-MenB PS (○). Different ranges for the X axis in the data are used, wherein monoclonal antibodies SEAM-3, SEAM-16 and SEAM-18 are shown at 0.0001 to 1 μg/ml, and monoclonal antibody SEAM-5 is shown at 0.1 to 100 μg/ml. The concentration of antibody sufficient to yield an OD of 0.5 after incubation with substrate varied considerably (compare binding of SEAM-5 to binding of SEAM-18).

Table 1 summarizes the respective concentration ranges of antibody required to yield an OD of 0.5 in an ELISA for each of the 39 SEAM monoclonal antibodies. The most likely explanation for the large heterogeneity in the values shown is differences in antibody avidity to NPr-MenB PS.

(c) Inhibition of Antibody Binding to NPr-MenB PS by Oligomers:

A competitive solid phase ELISA procedure was used to assess the ability of NPr-MenB oligomer inhibitors to inhibit binding of the monoclonal antibody molecules to solid phase NPr-MenB PS. The assay was performed as described above for the anti-NPr-MenB PS ELISA with the exception that the monoclonal antibodies were pre-diluted to concentrations to yield an OD of 0.5 to 1. The monoclonal antibodies were added to wells of replica plates, each containing one of the following soluble inhibitors to yield a final inhibitor concentration of 25 μg/ml: high molecular weight (HMW) NPr-MenB PS; or low molecular weight (LMW) NPr-MenB OS (having an average Dp of 3.8).

The plates were covered and incubated overnight at 4° C. On the following day, the wells were washed five times with cold Washing Buffer and then incubated for 3 hours at 4° C. with 100 μl/well of alkaline phosphatase conjugated anti-murine IgG, IgM and IgA polyclonal antibodies (Zymed) diluted 1:2000 in Diluting Buffer. The plates were then washed with cold Washing Buffer, and 100 μl of freshly prepared substrate (p-Nitrophenyl phosphate, Sigma) diluted to 1 mg/ml in Substrate Buffer was added to each well. Absorbance values at 405 nm were measured after approximately 30 minutes. Percent inhibition was calculated as compared to binding in the absence of inhibitor.

FIG. 2 depicts the inhibition of binding of four representative anti-NPr-MenB PS monoclonal antibodies (SEAM-2, SEAM-3, SEAM-16 and SEAM-18) to solid phase NPr-MenB PS by either 25 μg/ml of soluble high molecular weight (HMW) NPr-MenB PS inhibitor (■), or 25 μg/ml of low molecular weight (LMW) NPr-MenB oligosaccharide (average Dp of 3.8) inhibitor (□).

The HMW NPr-MenB PS inhibitor provided approximately 75% to 95% inhibition in all monoclonal antibodies tested. Differences in fine antigenic specificity in the monoclonal antibodies are evident from the different respective patterns of inhibition with the LMW inhibitor tested. For example, binding of SEAM-3 and SEAM-18 to NPr-MenB PS is completely inhibited by the soluble LMW inhibitor of NPr-MenB PS. In contrast, SEAM-2 and SEAM-16 are not significantly inhibited by the oligomers (less than 20%). The results of LMW NPr-MenB OS inhibition for all of the monoclonal antibodies are depicted in Table 1. In addition, as described below, other differences in the fine antigenic specificity of the monoclonals are evident by the differences observed in cross-reactivity to NAc-MenB PS in ELISA and differences in binding to host polysialic acid.

(d) Cross-Reactivity with NAc-MenB PS:

The monoclonal antibodies were evaluated for their ability to cross-react with the NAc-MenB polysaccharide as demonstrated by direct binding to NAc-MenB PS in a solid phase ELISA format. The method used was similar to that described above for the NPr-MenB PS ELISA, with the exception that NAc-MenB PS-ADH was used as the solid phase antigen instead of biotinylated NPr-MenB PS.

50 µl aliquots of various dilutions of the monoclonals were added to wells of replicate plates containing either 50 µl of Diluting Buffer or 50 µl of Diluting Buffer containing 50 µg of soluble NAc-MenB PS per ml (for a final inhibitor concentration of 25 µg/ml). The plates were then covered and incubated overnight at 4° C. On the following day, the wells were washed five times with cold Washing Buffer and then incubated for 3 hours at 4° C. with 100 µl/well of alkaline phosphatase conjugated anti-murine IgG, IgM and IgA polyclonal antibodies (ZYMED) diluted 1:2000 in Diluting Buffer. The plates were then washed with cold Washing Buffer, and 100 µl of freshly prepared substrate (p-Nitrophenyl phosphate, SIGMA) diluted to 1 mg/ml in Substrate Buffer was added to each well. Absorbance values at 405 nm were measured after approximately 30 minutes.

Figure 3:
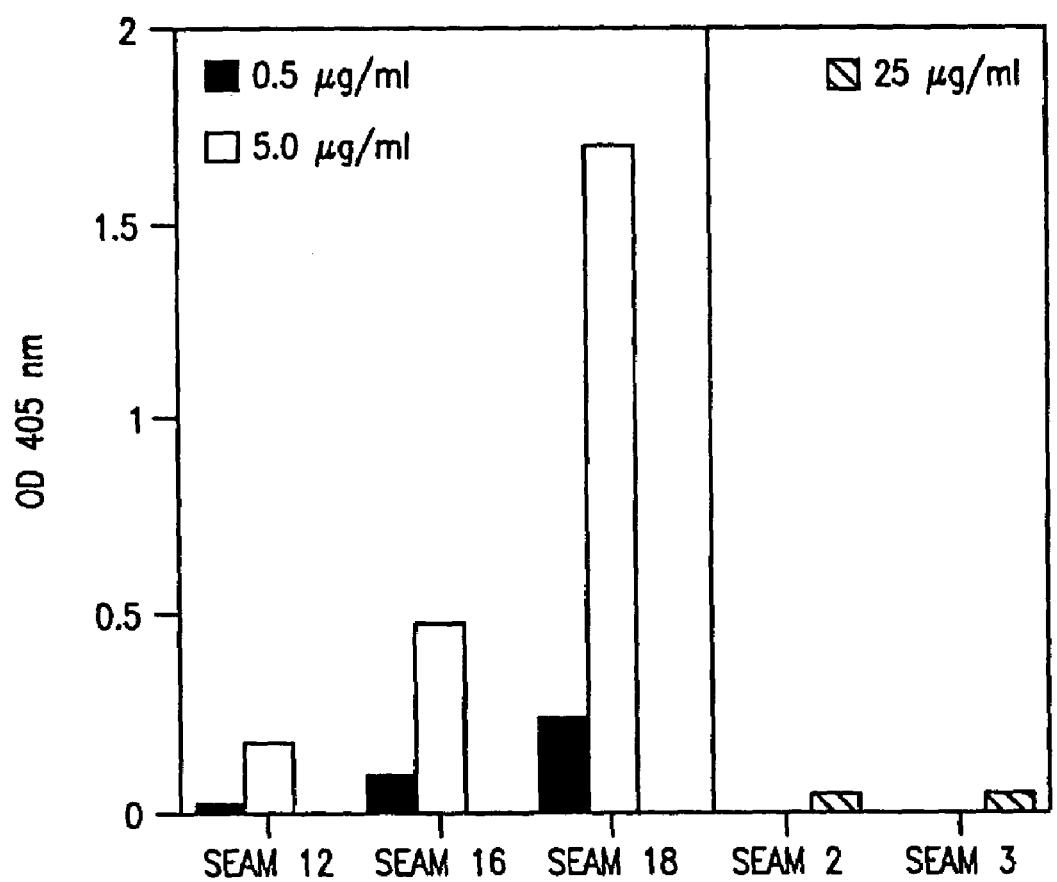

FIG. 3 depicts the binding of five representative anti-NPr-MenB PS monoclonal antibodies (SEAM-12, SEAM-16, SEAM-18, SEAM-2, and SEAM-3) to the solid phase NAc-MenB PS. As can be seen, three of the antibodies, SEAM-12, SEAM-16 and SEAM-18, showed significant binding when tested at 0.5 and/or 5 µg/ml of antibody. Two other antibodies, SEAM-2 and SEAM-3, previously shown to be negative in a screening assay, were confirmed as negative when tested at 5-fold higher concentrations (25 µg/ml of antibody). The cross-reactivity of each of the 39 monoclonal antibodies with the NAc-MenB PS was scored over a range of (+++) for highly cross reactive, to (0) for non cross-reactive. The results are depicted in Table 1. As can be seen, sixteen of the monoclonal antibodies cross-reacted with the NAc-MenB PS, and four minimally cross reacted (±) (FIG. 1). Specificity of the cross-reactivity of these twenty positive, or weakly positive monoclonal preparations was confirmed by inhibition of binding using soluble NAc-MenB PS. The 26 non cross-reactive monoclonal antibodies showed no significant binding to solid phase NAc-MenB PS when tested at antibody concentrations up to 25 µg/ml.

(e) Bacterial Binding Assay:

The ability of the anti-N-Pr meningococcal B polysaccharide antibodies to bind to the surface of pathogenic strains of *N. meningitidis* Group B was determined using flow cytometric detection of indirect immunofluorescence assay. Two fully encapsulated meningococcal B test organisms were used, strain 8047 (the strain used to measure bactericidal activity, see below) and NmB. A third unencapsulated strain, M7, which is a transposon-containing mutant of NmB (Stephens et al. (1991) *Infect. & Immun.* 59:4097–4102) was used as a negative control for specificity of antibody binding to the capsular polysaccharide. Bacterial cells grown to mid-log phase in Mueller-Hinton broth and 0.25% glucose were harvested and resuspended in Blocking Buffer at a density of ~$10^6$ cells per ml. The monoclonal antibodies (concentration of 10 or 100 µg/ml) were then added and allowed to bind to the cells on ice for 2 hours. Following two washes with Blocking Buffer, the cells were incubated with FITC-conjugated F(ab')$_2$ fragment goat anti-mouse IgG (H+L) (Jackson Immune Research, West Grove, Pa.), fixed with 0.25% formaldehyde in PBS buffer, and analyzed by flow cytometry.

Positive control antibodies included meningococcal-specific serotyping and subtyping monoclonal antibodies (MN2C3B, MN16C13F4, RIVM, Bilthoven, the Netherlands). The negative control consisted of a mouse IgG monoclonal antibody of irrelevant specificity.

FIGS. 4A–4G show the results from a representative experiment. Monoclonal antibodies SEAM-3 and SEAM-18 show strong capsular-specific binding to both encapsulated test strains. (FIGS. 4C and 4D, respectively) in this indirect fluorescence flow cytometry assay. In contrast, monoclonal antibodies SEAM-9 and SEAM-10 were negative in this assay (FIGS. 4E and 4F). As summarized in Table 1, twenty-four of the anti-N-Pr meningococcal B polysaccharide antibodies showed evidence of bacterial binding when tested at 100 µg/ml. Two additional antibodies showed evidence of minimal binding to both encapsulated and non-encapsulated mutant strains. Bacterial binding of these antibodies was scored as indeterminant (i). See, for example, the binding of SEAM-7 depicted in FIG. 4G.

(f) Complement-Mediated Bactericidal Activity:

A bactericidal assay was conducted using the methods described by Mandrell et al. (1995) *J. Infec. Dis.* 172:1279, with the following modifications: the organism was grown in Mueller-Hinton broth containing 0.25% glucose; and serum diluting buffer consisted of Gey's buffer instead of barbitol buffer. In several experiments, different sources of complement were used: these included two different infant rabbit serum pools (referred to as Rab C I and Rab C II) and human agammaglobulinemic serum (referred to as Hu C).

The percent survival of *N. meningitidis* strain 8047 when incubated with different concentrations of antibody and 20% complement is shown for four representative monoclonal antibodies (FIGS. 5A–5D). Each antibody shown was tested with three different complement sources: infant rabbit serum pool I (▲), infant rabbit serum pool II (●), and human agammaglobulinemia (○). For SEAM-5 and SEAM-12, a similar dose response for each antibody was observed for each of the three complement sources. In contrast, SEAM-18 required higher antibody concentrations to elicit bacterial killing in the presence of human complement than were required with either source of rabbit complement. SEAM-3 showed effective killing when tested with the two rabbit complement sources, and no activity with the human complement source. The ability of each of the monoclonal antibodies to activate complement-mediated bacterial lysis is reported in Table 1. There are examples of bactericidal antibodies that cross react with NAc-MenB PS by ELISA (e.g., SEAM-18, SEAM-30, and SEAM-35). There also are examples of bactericidal antibodies that show no cross-reactivity with NAc-MenB PS (e.g., SEAM-2, SEAM-5, SEAM-7, and SEAM-8).

(g) Opsonic Activity:

Opsonic activity of the monoclonal antibodies can be measured by a variety of established methods. Sjursen et al. (1987) *Acta Path. Microbiol. Immunol. Scand., Sec. C*

95:283, Halstensen et al. (1989) *Scand. J. Infect. Dis.* 21:267, Lehmann et al. (1991) *APMIS* 99:769, Halstensen et al. (1991) *NIPH Annals* 14:157, Fredlund et al. (1992) *APMIS* 100:449, Guttormsen et al. (1992) *Infect. Immun.* 60:2777, Guttormsen et al. (1993) *J. Infec. Dis.* 167:1314, Bjerknes et al. (1995) *Infect. Immun.* 63:160, and Hayrinen et al. (1995) *J. Infect. Dis.* 171:1481.

In one opsonization assay, *N. meningitidis* freshly grown on GN agar plates (Greiner Labortechniek, Greiner BV, Alphen a/d Rijn, Netherlands) at 37° C. was used to inoculate 8 ml of Mueller Hinton broth (Difco, Detroit, Mich.) to obtain an initial OD of 0.1. The bacteria were grown to log phase (660 nm absorbance of 0.75–0.85) with vigorous shaking. The cells were transferred to sterile plastic tubes with caps and centrifuged for 10 minutes at 3500 rpm.

Cells were fixed by adding 4 ml of 70% ethanol and incubating for at least 1 hour 4° C. The fixed cells were again pelleted by centrifugation for 10 minutes at 3500 rpm and resuspended in sterile phosphate buffered saline (PBS) to yield an OD of 1.0. The cell suspension (1.35 ml) was added to an eppendorf tube and centrifuged for 5 minutes at 10,000 rpm. The supernatant was discarded, and another 1.35 ml was added to the same tube followed by centrifugation to yield $1 \times 10^9$ cells per tube. A 1.0 mg/ml solution of fluorescein isothiocyanate (FITC) in PBS (Sigma, St. Louis, Mo.) was prepared and sonicated for 5 minutes, then centrifuged for 5 minutes at 10,000 rpm. The FITC-PBS solution (50 µl) was added to each tube of bacteria and then incubated for 1 hour at 37° C. with slight agitation. PBS (950 µl) was added to each tube and centrifuged for 2 minutes at 10,000 rpm. The pellet was washed once with 1 ml of PBS and once with 1 ml of BSA-Hanks balanced salt solution (BSA-HBBS). The FITC labelled meningococci were reconstituted in 1% BSA-HBBS and divided into 100 µl aliquots which were stored at −20° C. until use in the assay.

Human polymorphic nuclear cells (PMN) were isolated from the peripheral blood of healthy adults in heparin-containing tubes (Becton Dickinson, Mountain View, Calif.). A volume of 10 ml of blood was diluted with an equal amount of phosphate buffered saline (PBS; pH 7.4) and layered on a Ficoll histopaque gradient consisting of 10 ml of Ficoll Paque™ (Pharmacia, Uppsaila, Sweden) on top of 12 ml of histopaque (density 1.119, Sigma Diagnostics, St. Louis, Mo.). After centrifugation at 400×g for 20 minutes at room temperature, the PMN were collected from the upper part of the histopaque and ice cold RPMI medium (Roswell Park Memorial Institute, NY) containing 1% gelatin was added. Cells were centrifuged at 250×g and the residual erythrocytes were lysed by resuspending the cells in 9 ml of ice cold distilled water. After 1 minute, concentrated PBS and RPMI-gelatin was added to make the cell suspension isotonic. The PMN were centrifuged and resuspended in RPMI medium to a density of $1 \times 10^7$/ml. The purity and viability of the PMN was greater than 95%.

To a microtiter plate was added appropriate dilutions of monoclonal antibody to be tested (diluted in BSA-HBBS), 5 µl of 10% human complement (in BSA-HBBS), and 25 µl of FITC-labelled bacteria suspension to yield a total volume of 50 µl. Selected antibodies were tested without complement, and with up to three different complement sources: normal pooled human serum; agammaglobulinemic serum; and infant rabbit serum, varying the complement concentration from 1 to 10%. Each assay included a positive and negative antibody control, as well as a complement, non-opsonization and a cells-only control. The opsonization reaction was allowed to proceed for 30 minutes at 37° C. on a shaker before terminating the reaction by placing the microtiter plate on ice.

Phagocyte cell suspension (50 µl) was added to a final concentration of $5 \times 10^6$ cells/ml. This gives a ratio of bacteria to phagocytes of 10:1. Phagocytosis was allowed to proceed for 30 minutes at 37° C. on a shaker, after which time it was placed on ice. Cold BSA-HBBS (100 µl) was added to each well. The plates were centrifuged for 10 minutes at 1100 rpm. Supernatants were aspirated from the wells and the cells were washed twice more with 150 µl of cold BSA-HBBS. Cold BSA-HBBS (150 µl) was then added, and the resulting cell suspensions were transferred to sterile tubes. A solution of 2% paraformaldehyde (Polysciences, Inc., Warrington, Pa.) in PBS was added to fix the cells. The samples were then analyzed by indirect florescence flow cytometry.

The results of the opsonization experiments for sixteen representative SEAM monoclonal antibodies are reported in Table 1. All antibodies found to be opsonic were also bactericidal in the assay described above using at least one of the complement sources. However, as can be seen in Table 1, there are examples of antibodies that were bactericidal but not opsonic (see, e.g., SEAM-2, SEAM-5, SEAM-7, SEAM-16, and SEAM-41).

(h) Evaluation of Autoreactivity:

Partially purified tissue culture supernatants containing the 39 SEAM monoclonal antibodies were evaluated for autoreactivity to host polysialic acid. In one assay, the monoclonal antibodies were assessed for their ability to cross-react with the human neuroblastoma cell line CHP-134 (Livingston et al. (1988) *J. Biol. Chem.* 263:9443) using flow cytometric detection of indirect immunofluorescence. In this assay, the CHP-134 cells, which express long chain polysialic acid (PSA) associated with neuronal cell adhesion molecule (NCAM) on their surface, serve as cellular markers for human PSA antigens. In control experiments, nearly confluent cell cultures were collected in 50 ml centrifuge tubes and centrifuged at 1000×g. After the supernatant was decanted, 5 ml of Blocking Buffer was added to resuspend the cells. The cells were then counted in a hemacytometer, and divided into two equal aliquots. One aliquot was incubated for 2 hours at ambient temperature with exoneuraminidase (10 units/$10^8$ cells, SIGMA Chemical Co., Saint Louis, Mo.); the other aliquot was treated identically but without enzyme. After incubation, the cells from each aliquot were distributed among individual reaction tubes so that each tube contained $10^6$ cells. To wash the cells, 2 ml of Blocking Buffer was added to each reaction tube, the tubes centrifuged at 1000 rpm in a Sorvall RT-600B for 6 minutes at 20° C., and the supernatant aspirated off. The washed cells were incubated for 2 hours in a total volume of 200 µl on ice with either no antibody, or the indicated concentration (usually 10 or 100 µg/ml) of the test antibody (i.e., SEAM MAbs).

Control antibodies in the assay included: (1) an IgG monoclonal antibody of irrelevant specificity (VIIG10, as a negative control); (2) an IgM anti-polysialic acid monoclonal antibody (2-1B, as a positive control); and (3) an anti-CD56 monoclonal antibody specific for the protein backbone of NCAM (Immunotech, Marseille, France). Blocking Buffer (2 ml) was added to each reaction tube, and the tubes were centrifuged at 1000 rpm in the SORVALL RT-600B for 6 minutes at 20° C. Following centrifugation, the supernatant was aspirated off and the cells incubated for 1 hour at ambient temperature with 150 µl of fluorescein isothiocyanate (FITC)-conjugated F(ab')$_2$ fragment goat anti-mouse IgG (H+L) (diluted to 4 µg/ml) (Jackson Immune Research, West Grove, Pa). After washing with Blocking Buffer, 400 µl of 0.25% formaldehyde in PBS buffer (50 mM sodium phosphate, pH 7.0, 150 mM sodium chloride) was added to the cells, and the cells were analyzed by flow cytometry using a FACSCAN™ cell sorter (Becton-Dickinson, Mountain View, Calif.).

All antibodies were tested at final concentrations of 10 and 100 µg/ml of antibody in replicate, using untreated cells, and cells that had been pre-treated with neuraminidase. This treatment cleaves the surface polysialic acid and provides a control in the assay for specificity of antibody binding to polysialic acid. In a typical experiment (FIGS. 6A–6I), cells incubated without primary antibody, or with a control monoclonal antibody having an irrelevant antigenic specificity, show very little fluorescence (approximately 98% of the cells have <10 units of fluorescence, FIG. 6A). In contrast, virtually all cells treated with the anti-NAc MenB PS monoclonal antibody, 2-1B, fluoresce strongly (FIG. 6B, left). This fluorescence is decreased to control levels when the antibody is incubated with cells that had been pre-treated with neuraminidase (FIG. 6B, right). Similarly, cells treated with anti-CD56 fluoresce strongly (FIG. 6C). With this antibody, the fluorescence is unaffected by pre-treatment of the cells with neuraminidase since the CD56 determinant is located in the protein backbone of NCAM and is unaffected by the removal of polysialic acid with neuraminidase.

The SEAM-5 antibody gives no detectable binding when tested at 100 µg/ml (FIG. 6D), and is considered as negative in this assay. The SEAM-35 antibody shows strong polysialic acid-specific binding when tested at 10 or 100 µg/ml (FIGS. 6E and 6F), and is considered positive. A few anti-NPr MenB PS monoclonal antibodies show binding when tested at 100 µg/ml, but appear to be negative when tested at 10 µg/ml (see, e.g., SEAM-12 in FIGS. 6G and 6H). Such antibodies are considered minimally autoreactive for the purposes of this application. A rare antibody appeared to have weak reactivity with the neuroblastoma cell line that was unaffected by the by pre-treatment of the cells with neuraminidase (see SEAM-7, FIG. 6I). The autoreactivity of such antibodies with polysialic acid was scored as indeterminant in the assay, and these antibodies were also considered to have minimal autoreactivity to host PSA for purposes of this application.

Table 1 summarizes the autoantibody activity of each antibody as determined in this indirect fluorescence flow cytometry assay. Cross-reactivity with polysialic acid antigens expressed in CHP-134 cells was closely correlated with the cross-reactivity of the antibodies with NAc-MenB PS in the ELISA assay. As shown in Table 1, monoclonal antibodies that did not cross react with NAc-MenB PS in the ELISA also did not bind to CHP-134 cells, while all of the antibodies that cross-reacted with NAc-MenB PS in the ELISA also cross-reacted with PSA. This correlation between the two assays was not unexpected since the polysaccharide covalent structure of NAc-MenB PS and the host PSA is reported to be the same.

EXAMPLE 5

Passive Immunization Using SEAM Monoclonal Antibody Compositions

In order to assess the ability of the above-characterized SEAM monoclonal antibodies to provide passive protection against bacterial challenge, the following immunization study was carried out.

Animals: Outbred infant SPF (specific pathogen-free) albino Wistar rats were obtained from the Helsinki University Animal Center (Helsinki, Finland).

Bacterial Strains: *Neisseria meningitidis* group B strain IH 5341, a human patient isolate with MenB:15:p1.7, 16 phenotype, plus 1 to 2 additional other group B bacterial strains (e.g. M355; B:15:P1.15) were used. All bacteria strains were rat passaged five times and stored in skim milk at −70° C. For each experiment, a fresh inoculum was taken from the stock and cultivated on gonococcal (GC) medium base (GC-agar II Base, Becton Dickinson, Mountain View, Calif.) supplemented with ISOVITALEX, L-tryptophan and hemoglobin. After incubation overnight at 37° C. in 5% $CO_2$, several colonies were inoculated into a culture flask containing 20 ml of brain-heart infusion broth and incubated at 37° C. in a rotatory shaker at 150 rpm until the optical density (Klett 90) corresponded to $10^8$ cfu/ml. The cultures were then diluted in phosphate buffered saline (PBS) corresponding to $10^6$ cfu/ml for use. The actual number of viable bacteria in a challenge dose was determined by counting the cfu after serial dilution of the suspension in PBS and plating on proteose peptone agar.

Immunizations: In each experiment 3–4 litters of 4–6 day old infant rats were randomly selected and divided into experimental groups of 6 animals each and injected intraperitoneally with either a SEAM monoclonal antibody composition (in 0.9% saline), saline solution (0.9%), or control antibodies. In each group, three animals were inoculated with the SEAM antibodies (at doses of 0.4 µg, 2 µg, and 10 µg, respectively), two animals were used as negative controls (one received injection with saline alone while the other received injection with a monoclonal antibody of irrelevant specificity), and a positive animal received an injection of an anti-Men B polysaccharide antibody.

Bacterial Challenge: One to two hours after the initial injection, the infant rats received a bacterial challenge injection intraperitoneally of $10^5$ *Neisseria meningitidis* group B bacteria of the strain IH 534 (rat passaged five times) in a final volume of 100 µl. Six hours after bacterial inoculation, bacteremia and meningitis development was assessed by culturing blood and cerebrospinal samples taken from the infant rats.

The results of the study (protection from *N. meningitidis* bacteremia) for six representative SEAM monoclonal antibodies (SEAM-5, SEAM-7, SEAM-8, SEAM-10, SEAM-12, and SEAM-18) are depicted below in Table 4. As can be seen, the SEAM-12 and SEAM-18 antibodies are strongly protective, the SEAM-7 and SEAM-8 antibodies partially protective, with the SEAM-5 and SEAM-10 antibodies providing no protection up to a dose of 10 µg/pup.

TABLE 2

| SEAM Mab | Blood (positives/all) | Blood Titer in cfu/ml × $10^5$ (% of negative control) | Cerebral Spinal Fluid (positives/all) |
|---|---|---|---|
| Dose: 10 µg/pup | | | |
| 5 | 5/6 | 0.63 (31%) | 3/6 |
| 7 | 0/6 | <0.01 (<1%) | 0/6 |
| 8 | 1/6 | <0.01 (<1%) | 0/6 |
| 10 | 6/6 | 10.67 (>100%) | 4/6 |
| 12 | 0/6 | <0.01 (<1%) | 0/6 |
| 18 | 0/6 | <0.01% (<1%) | 0/6 |

TABLE 2-continued

| SEAM Mab | Blood (positives/all) | Blood Titer in cfu/ml × $10^5$ (% of negative control) | Cerebral Spinal Fluid (positives/all) |
|---|---|---|---|
| Dose: 2 µg/pup | | | |
| 5 | 6/6 | 0.37 (18%) | 2/6 |
| 7 | 4/6 | 0.04 (<1%) | 0/6 |
| 8 | 6/6 | 2.52 (>100%) | 4/6 |
| 10 | 6/6 | 10.35 (>100%) | 5/6 |
| 12 | 1/6 | 0.01 (<1%) | 1/6 |
| 18 | 1/6 | <0.01% (<1%) | 1/6 |
| Dose: 0.4 µg/pup | | | |
| 5 | 5/5 | 5.65 (>100%) | 4/5 |
| 7 | 6/6 | 9.28 (>100%) | 5/6 |
| 8 | 6/6 | 1.50 (63%) | 4/6 |
| 10 | 6/6 | 10.67 (>100%) | 4/6 |
| 12 | 6/6 | 9.51 (76%) | 5/6 |
| 18 | 5/5 | 3.51% (>100%) | 3/5 |

EXAMPLE 6

Identification of Peptide Mimetics of MenB Antigen Using SEAM Monoclonal Antibodies The following procedures were carried out in order to identify peptide mimetics that interact with the SEAM monoclonal antibodies of the present invention. Phage display peptide libraries were constructed in an M13 vector using techniques known to those skilled in the art. Adey et al. (1996) "Construction of Random Peptide Libraries in Bacteriophage M13," in *Phage Display of Peptides and Proteins*, Kay et al., eds., Academic Press, San Diego, Calif. Particularly, linear 8mers (L8), cyclic 6mers (C6) and single C (C1) peptides were displayed as N-terminal extensions of the pIII bacteriophage protein. The characteristics of the libraries are presented below in Table 3.

TABLE 3[a]

| Library | Randomized Segment[b,c] | Number of Sequences |
|---|---|---|
| Linear 8mer (L8) | A E X X X X X X X X G G (P)$_6$ ... | $2.5 \times 10^{10}$ |
| Cyclic 6mer (C6) | A E C X X X X X X C (P)$_4$ ... | $6.4 \times 10^7$ |
| Single C (C1) | A E X X X X X X X X G C (P)$_6$ ... | $2.5 \times 10^{10}$ |

[a]Peptides are displayed as fusions with M13 phage protein, pIII.
[b]X represents a random amino acid, all other are standard single letter code.
[c](P)$_4$ or (P)$_6$ refers to either four or six Proline residues, respectively.

Panning of the libraries was carried out using the techniques described by Smith et al. (1993) *Methods in Enzymology* 217:228, with the exception that the antibodies were absorbed directly to microtiter plates. 100 µl solutions containing representative monoclonal antibodies (1 µg/ml of SEAM-2, SEAM-3, SEAM-5, SEAM-7, SEAM-12, SEAM-16, SEAM-18, and SEAM-28), or a corresponding concentration of control antibodies (a murine anti-MenB PS-specific monoclonal (2-1B), a human anti-Hib PS monoclonal (ED8), and a murine monoclonal of irrelevant specificity (Laz2))were incubated overnight at 4EC in microtiter plates (IMMULON II). After washing the wells with PBS, Blocking Solution (5% (w/v) non-fat dry milk, 0.2% (w/v) TWEEN 20 (polyoxyethylenesorbitan monolaurate), 0.02% (w/v) sodium azide in PBS) was added to completely fill the wells, and the plates were then incubated at ambient temperature for 3 hours. The blocked plates were washed six times with PBS.

Approximately $10^{10}$ pfu of phage were added to triplicate wells in a total volume of 100 µl per well. The plates were incubated with the phage overnight at 40° C. Each well was then washed nine times with PBS, and the bound phage released by adding to each well 100 µl of 0.2 M glycine, HCl (pH 2.2) buffer and incubating at ambient temperature for 1 hour. The buffer solutions from respective triplicate wells were combined, and the pH adjusted to 8 by addition of 20 µl 1.5 M Tris (pH 8.8) buffer per 100 µl of solution. A freshly grown culture (2 ml) of *E. coli* (XL1-Blue) at a density of $OD_{550nm}$=0.4–0.6 in LB media containing 0.2% (w/v) maltose and 12 µg/ml tetracycline (LB-mal, tet media) was added to the combined solutions of released phage. The cells and phage were incubated at 37° C. for 20 minutes, after which 20 ml of media was added. The cells were grown overnight at 37° C., then pelleted by centrifugation (5000×g for 10 minutes). The supernatant was filtered through a 0.2 µm membrane, and the phage precipitated by adding 0.15 volumes of 20% (w/v) polyethylene glycol 8000, 4 M NaCl., and allowing the mixture to stand at 4° C. overnight. Precipitated phage were collected by centrifugation (10,000×g for 10 minutes), and then resuspended in 20 ml PBS (approximately $10^{12}$ pfu/ml).

Each panning was repeated 3 or 4 times for each screen. Finally, phage released from the final pan were used to infect XL1-Blue cells and several serial dilutions were plated directly on LB-agar plates. Individual plaques were selected and amplified in 5 ml cultures of XL1-Blue (LB-mal, tet media). DNA from the phage was prepared using QIA8-Prep™ columns (Quiagen) and sequenced using a Sequenase™ kit (Amersham) according to the manufacturer's instructions.

A total of 67 unique peptide sequences (Peptides Pep 1–Pep 67) were selected by the SEAM monoclonal antibodies. These peptide sequences are depicted in FIG. 7 as SEQ ID NOs. 1–67. Of these sequences, 13 were identified on more than occasion (Table 4). With one exception, none of the sequences selected by the control antibodies (2-1B, ED8 and Laz2) were identical or significantly homologous to those selected by the SEAM monoclonal antibodies. The single exception (SEQ ID NO. 9) was selected by both SEAM-3 and the Laz2 control antibody. However, this result was possibly due to a cross-contamination between reagents since both experiments were conducted at the same time.

TABLE 4

| Antibody | Peptide Sequence | Number of Identical Isolates |
|---|---|---|
| SEAM-2 | Pep 10 (SEQ ID NO. 10) | 3 |
| SEAM-2 | Pep 13 (SEQ ID NO. 13) | 2 |
| SEAM-2 | Pep 14 (SEQ ID NO. 14) | 2 |
| SEAM-3, 16, 18 | Pep 1 (SEQ ID NO. 1) | 37 |

TABLE 4-continued

| Antibody | Peptide Sequence | Number of Identical Isolates |
|---|---|---|
| SEAM-5 | Pep 2 (SEQ ID NO. 2) | 3 |
| SEAM-7 | Pep 3 (SEQ ID NO. 3) | 5 |
| SEAM-7, 18 | Pep 4 (SEQ ID NO. 4) | 2 |
| SEAM-7, 18 | Pep 5 (SEQ ID NO. 8) | 2 |
| SEAM-12 | Pep 6 (SEQ ID NO. 6) | 4 |
| SEAM-18 | Pep 7 (SEQ ID NO. 7) | 3 |
| SEAM-18 | Pep 12 (SEQ ID NO. 12) | 4 |
| SEAM-28 | Pep 8 (SEQ ID NO. 8) | 2 |
| SEAM-28 | Pep 67 (SEQ ID NO. 67) | 2 |

EXAMPLE 7

Characterization of the Peptide Mimetics

For characterization of the antibody binding to synthetic peptides, the partially purified monoclonal antibodies were purified further on a BIOCAD® perfusion chromatography workstation using a Poros G/M protein G column (4.6mm× 100 mm) with a column volume of 1.7 ml (PerSeptive Biosystems, Framingham, Mass.). The protein G column was equilibrated with 10 column volumes of PBS buffer. Monoclonal antibody preparations (2 ml) from either ascites or tissue culture resuspended in PBS were injected onto the protein G column. After washing with 5 column volumes of PBS buffer, monoclonal antibody was eluted from protein G column with a 0.2 M Glycine-HCl, 150 mM sodium chloride (pH 2.5) buffer. The eluted antibodies were monitored with internally equipped spectrophotometric detectors at both 220 nm and 280 nm, and the elution peak collected and stored at 4° C. The pH of each 1 ml fraction was raised to 8.0 by adding 100 µl of 1.5 M Tris (pH 8.8) immediately upon collection. Concentrations of the purified monoclonal antibodies were determined with a spectrophotometer from absorbance at 280 nm using an extinction coefficient of 0.71 $mg^{-1}$ ml $cm^{-1}$.

An ELISA was used to determine the ability of anti-NPr-MenB PS antibodies to recognize synthetic peptides corresponding to selected peptide mimetic sequences identified in Table 4. Synthetic peptides were purchased from Biosynthesis (Lewisville, Tex.). To facilitate absorption to the ELISA plate, the peptides were modified by the addition at the amino terminus of a hydrophobic tail (Lauryl-GLY-GLY). Further, the peptides were carboxyl-terminal amides. The synthetic peptides (1 mg) were resuspended in 100 µl of dimethyl sulfoxide (Sigma, St. Louis, Mo.) and an aliquot was then diluted further in 50 mM Hepes (Fisher Scientific, Pittsburgh, Pa.) pH 8.0, 150 mM NaCl (Sigma, St. Louis, Mo.) and 0.02% sodium azide (Sigma, St. Louis, Mo.) to a peptide concentration of 10 µg/ml. Microtiter plates (Immulon 2®; Dynatech Laboratories Inc., Chantilly, Va.) containing 100 µl/well of a 10 µg/ml peptide solution in 50 mM Hepes buffer were incubated overnight at 4° C. After washing the plates 3 times with phosphate buffered saline (PBS, pH 7.4), the wells were filled with 200 µl of Blocking Buffer and incubated for 1–2 hours at room temperature to block non-specific binding sites. The plates were then washed 5 times with Washing Buffer.

Various dilutions of the SEAM monoclonal antibodies (50 µl) to be tested for peptide binding were added to duplicate plates containing either 50 µl of Diluting Buffer or 50 µl of Diluting Buffer containing 50 µg of soluble NPr-MenB PS per ml (final inhibitor concentration of 25 µg/ml). The plates were then covered and incubated overnight at 4° C. The following day plates were washed 5 times with Washing Buffer, and then incubated for 3 hours at 4° C. with 100 µl/well of alkaline phosphatase-conjugated anti-mouse polyclonal antibody, IgA+IgG+IgM (Zymed, South San Francisco, Calif.) diluted 1:2000 in Diluting Buffer. The plates were then washed 5 times with Washing Buffer, and 100 µl of freshly prepared substrate (p-nitrophenyl phosphate, Sigma, St. Louis, Mo.) diluted to 1 mg/ml in Substrate Buffer was added to each well. Absorbance values were measured after 30 minutes at 405 nm.

Representative binding data to the tethered Pep 4 and Pep 8 are shown in FIGS. 8-A and 8-B, respectively. Several of the SEAM anti-NPr-MenB PS monoclonal antibodies recognize these two peptides. In contrast, irrelevant mouse monoclonal antibodies of the same isotypes show no binding in this assay (data not shown). For some of the SEAM anti-NPr-MenB PS monoclonal antibodies, the addition of NPr-MenB PS at 25 µg/ml completely inhibited binding of the antibody to the peptides (e.g., SEAM-3). For other antibodies, there is either partial inhibition of binding (e.g., SEAM-16 and SEAM-18), or no inhibition (SEAM-5). As summarized in Table 5, there is a close correspondence between the concentration-dependent binding of the SEAM anti-NPr-MenB PS monoclonal antibodies to NPr-MenB PS and the respective binding to particular synthetic peptides. See, for example, the relative binding of antibodies SEAM-3, SEAM-5, SEAM-7, SEAM-16, and SEAM-18 to NPr-MenB PS and to Pep 8.

TABLE 5

Relative Binding of SEAM Monoclonal Antibodies

| | To NPr-MenB PS[a] | To Synthetic Lauryl-GLY-GLY-Peptides[b] | | | | | | | |
|---|---|---|---|---|---|---|---|---|---|
| | | Pep 1[c] | Pep 2 | Pep 3 | Pep 4 | Pep 6 | Pep 7 | Pep 8 | Pep 9 |
| SEAM-3 | 0.004 | — | — | 0.016 | 0.014 | — | — | 0.009 | 0.019 |
| SEAM-5 | 5 | — | 47 | 3 | 3 | — | — | 3 | 23 |
| SEAM-7 | 15 | 81 | 80 | 11 | 6 | 25 | — | 11 | 60 |

TABLE 5-continued

| | Relative Binding of SEAM Monoclonal Antibodies | | | | | | | | |
|---|---|---|---|---|---|---|---|---|---|
| | To NPr-MenB PS[a] | To Synthetic Lauryl-GLY-GLY-Peptides[b] | | | | | | | |
| | | Pep 1[c] | Pep 2 | Pep 3 | Pep 4 | Pep 6 | Pep 7 | Pep 8 | Pep 9 |
| SEAM-16 | 0.08 | 0.2 | — | — | 0.2 | — | — | 0.06 | — |
| SEAM-18 | 0.14 | 0.8 | — | 0.8 | 0.4 | 1 | — | 0.2 | — |

[a]In μg/ml of monoclonal antibody, (—) indicates no detectable binding in the ELISA.
[b]Concentration of monoclonal antibody required to give an OD of 0.5 at 405 nm after 30 min. incubation with substrate in ELISA.
[c]See FIG. 7 for the amino acid sequences of peptides Pep 1–Pep 4 and Pep 6–Pep 9.

EXAMPLE 8

Preparation of Peptide Mimetic Vaccine Compositions

Vaccine compositions containing synthetic peptides corresponding to the above-described peptide mimetic sequences were prepared as follows.

Preparation of OMP Vesicles. OMP vesicles were prepared from the capsular-deficient mutant strain of *Neisseria meningitidis* Group B (Strain M7), using a combination of the techniques described by Lowell et al. (1988) *J. Expt. Med.* 167:658–663 and Zollinger et al. (1979) *J. Clin. Invest.* 63:836–848. In brief, *Neisseria meningitidis* strain M7 (a noncapsular mutant strain derived from NmB), from an overnight culture on chocolate agar plates incubated at 37° C., was used to inoculate two 500 ml flasks of sterile Frantz medium (10.3 g of $Na_2HPO_4$, 10 g of casamino acids (Difco, Detroit, Mich.), 0.36 g of KCl, 0.012 of cysteine-HCl (SIGMA, St. Louis, Mo.), and 25 ml of 40% glucose-40 mM $MgSO_4$ (SIGMA, St. Louis, Mo.) in 1 L of water, pH 7.4). The bacteria were grown from an initial OD of 0.1–0.2 to log phase (OD of 0.75–0.85) on a shaker at 180 rpm for 6–8 hours. The bacteria were inactivated with 0.5% phenol solution for one hour at room temperature. The cells were harvested by centrifuging for 30 minutes at 3000×g. The supernatant was decanted, and the cells were washed twice with PBS. The resultant pellet was stored at −20° C.

The bacteria were then resuspended in 15 ml buffer containing 0.05 M Tris-HCl, 0.15 M NaCl and 0.01M EDTA (pH 7.4), and then warmed to 56° C. for 30 minutes. After cooling to room temperature, the suspension was sheared in a POLYTRON (Kinematica GmbH., Luzern, Switzerland) at full speed for 3 minutes and then centrifuged at 16000×g for 15 minutes. The resulting pellet was resuspended with 10 ml buffer (500 mM sodium chloride, 50 mM sodium phosphate), and treated with 5 ml of Detergent Solution (10% sodium deoxycholate (DOC) (Calbiochem, La Jolla, Calif.), 0.15 M glycine (Biorad, Hercules, Calif.) and 30 mM ethylenediaminetetraacetic acid (EDTA) (SIGMA, Saint Louis, Mo.). The suspension was centrifuged at 16,000×g for 15 minutes. The supernatant was then collected and centrifuged at 100,000×g for 2 hrs. A pellet containing the outer membrane protein preparation was resuspended in 10 ml of water and stored at 4° C.

The 10 ml suspension of outer membrane protein was retreated with 5 ml of the Detergent Solution, and then warmed to 56EC for 30 minutes. After cooling, lipopolysaccharide (LPS) was removed from the outer membrane protein by chromatography, 2 ml at a time, using a 2 cm×20 cm SEPHADEX G-100 column (Pharmacia Fine Chemicals, Piscataway, N.J.) in a second detergent solution (1% DOC, 0.05 M glycine, and 0.005 M EDTA, pH 8.8). The peak fractions were collected, warmed to 30EC and sterile-filtered through a 0.2 μm membrane filter directly into 4 volumes of cold, filter-sterilized ethanol. This mixture was incubated at 4EC overnight. The resulting precipitate was collected by centrifugation at 16,000×g for 10 minutes, and resuspended in 1 ml of sterile distilled water. The resulting OMP preparation was soluble but slightly opalescent, and was stored at −60EC.

Preparation of Peptide/OMP Vesicles. Vaccines were prepared from peptides Pep 5 and Pep 8, or from a mixture of peptides Pep 1–Pep 9. To facilitate hydrophobic complexing of the peptides to the OMP vesicle, each peptide was modified by the addition at the amino terminus of a hydrophobic tail (Lauryl-GLY-GLY) and a carboxyl amide as described above for the ELISA. For each vaccine, 5 mg of peptide was dissolved in 100 μl dimethylsulfoxide (DMSO) (SIGMA, Saint Louis, Mo.). The resulting solution was diluted to 750 μl in buffer containing 50 mM 4-(-2-hydroxyethyl)-1-piperazineethanesulfonic Acid (Hepes), pH 8.0, and 1 M potassium ferricyanide (SIGMA, Saint Louis, Mo.). 7.5 μg of zwitterionic detergent (Empigen, Calbiochem, La Jolla, Calif.) was then added to the above peptide solution. After incubation at room temperature for 1 hour, each of the peptide solutions was combined with 250 μl of outer membrane protein (OMP) vesicles (20 mg/ml) for a total volume of 1 ml. The solution was heated to 75EC for 20 minutes. After cooling to room temperature, the OMP/Peptide mixture was added to a SLIDE-A-LYZER (Pierce, Rockford, Ill.) a dialysis cassette with a 10,000 molecular weight cut off, and dialyzed in 1 L PBS overnight. The PBS solution (1 L) was changed twice over 8 hours.

EXAMPLE 9

Immunization with OMP-Peptide Mimetic Vaccine Compositions

In order to assess the OMP-peptide vaccine compositions prepared in Example 8 above, the following study was carried out.

Animals: Balb/c and CD1 mice (Jackson Laboratory, Bar Harbor, Me.) were used for the immunogenicity studies. Mice were kept in quarantine for 2 weeks.

Vaccine Preparations: For the first injection, vaccine solutions (2 mg/ml total peptide/protein in PBS) were combined with equal volumes of complete Freund's adjuvant. (Sigma, St. Louis, Mo.) to yield a final concentration of 1 mg/ml of peptide/protein. For the subsequent injections, similar vaccine compositions were prepared using incomplete Freunds adjuvant. The respective compositions were forced back and forth through 2 syringes in order to obtain homogenous emulsions which were then used in the immunizations.

Immunizations: Each treatment group included 4 Balb/c mice and 4 CD1 mice. There were also control groups of 4 Balb/c and 4 CD1 mice that were not immunized. Individual treatment groups received doses of 5 μg or 50 μg of peptide, and 5 μg or 50 μg of OMP Vesicles, respectively. The vaccine composition was administered intraperitonealy (IP), in a total volume of 5 or 50 μl, respectively. Immunizations were repeated at 3 week intervals for a total of 3 immunizations. The animals were bled from the tail vein 1 and 4 weeks after the third immunization.

CD1 and Balb/c mice immunized with peptide Pep 8 complexed with OMP vesicles develop high anti-Pep 8 antibody responses as measured by ELISA in serum obtained 4 weeks post-third immunization. Representative data for the responses of the CD1 mice are shown in FIG. 9. Antibody binding to tethered Pep 8 is inhibited by soluble Pep 8 (Acetyl-[Pep 8]-Amide) but not by a soluble irrelevant peptide "R1" (Acetyl-GLN-TRP-GLU-ARG-THR-TYR-Amide (SEQ ID NO. 68)). Anti-Pep 8 antibodies also were elicited in mice immunized with a combination of nine peptides (peptides Pep 1–Pep 9/OMP), but not in mice immunized with Pep 5/OMP alone. This demonstrates the Pep 8-specific antibodies were elicited by Pep 8-containing immunogens.

FIG. 10 summarizes the cross-reactivity of the CD1 mouse immune sera with NPr-MenB PS or NAc-MenB PS in an ELISA assay. All three immunogens (Pep 5/OMP, Pep 8/OMP, and peptides Pep 1–Pep 9/OMP) appeared to elicit serum antibodies cross-reactive with NPr-MenB PS, which were not detected in the serum pool from the unimmunized control mice. However, the specificity of this antibody binding could not be confirmed since there was no significant inhibition observed in wells containing soluble NPr-MenB PS (data not shown). The ability of soluble Pep 8 (Acetyl-[Pep 8]-Amide) to inhibit binding of the anti-Pep 8 serum pools to the solid phase NPr-MenB PS also could not be verified since the presence of this peptide resulted in significant increase in antibody binding which was not detected in the presence of a soluble irrelevant peptide "R1" (Acetyl-GLN-TRP-GLU-ARG-THR-TYR-Amide (SEQ ID NO. 68)).

Data from characterization of the extensive collection of SEAM monoclonal antibodies indicate that the ability of an antibody to bind to NAc-MenB PS in an ELISA correlates with the presence of autoantibody activity as assessed by binding to PSA expressed by CHP-134 neuroblastoma cells (see Table 1). FIG. 11 summarizes the cross-reactivity of the CD1 mouse immune sera with NAc-MenB PS in an ELISA. None of the serum pooled from the peptide-vaccinated mice were positive in this assay. In contrast, a SEAM anti-NPr-MenB PS monoclonal antibody with known autoantibody activity was strongly positive in this assay when tested at 2.0 μg/ml. The lack of cross-reactivity of the anti-Pep antisera with NAc-MenB PS by ELISA indicates that these antibodies do not have PSA-specific autoantibody activity.

Complement-mediated bactericidal activity of pooled CD1 sera from mice immunized with either 5 μg or 50 μg of Pep 8/OMP vaccine is shown in FIGS. 12A and 12B, respectively. At both doses, the Pep 8-containing vaccine elicited serum antibodies that were able to mediate bacteriolysis of MenB strain 8047 in the presence of human complement. A portion of this antibody may have been elicited by the OMP vesicles used as an adjuvant. However, at serum dilutions of 1:1000, 50% or greater of the bactericidal activity was mediated by the anti-Pep 8 antibodies as demonstrated by inhibition of the reaction with Lauryl-GLY-GLY-Pep 8 at a final serum concentration of 100 μg/ml.

Thus, novel MenB PS antibodies, molecular peptide mimetics capable of eliciting bactericidal MenB antibody, and method for obtaining and using the same are disclosed. Although preferred embodiments of the subject invention have been described in some detail, it is understood that obvious variations can be made without departing from the spirit and the scope of the invention as defined by the appended claims.

Deposits of Strains Useful in Practicing the Invention

Deposits of biologically pure cultures of the following hybridoma cell lines were made with the American Type Culture Collection (ATCC), 10801 University Boulevard, Manassas, Va. 20110-2209. The accession numbers indicated were assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, and subject to an agreement between Chiron Corporation and the ATCC, which assures permanent and unrestricted availability of the progeny to one determined by the U.S. Commissioner of Patents and Trademarks to be entitled thereto according to 35 U.S.C. §122 and the Commissioner's rules pursuant thereto (including 37 C.F.R. §1.12 with particular reference to 886 OG 638). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these hybridomas, as well as the amino acid sequences of the antibody molecules encoded thereby, are incorporated herein by reference and are controlling in the event of any conflict with the description herein. A license may be required to make, use, or sell the deposited materials, and no such license is hereby granted.

| HYBRIDOMA | Deposit Date | ATCC No. |
|---|---|---|
| SEAM-3 | Aug. 16, 1996 | HB-12170 |
| SEAM-18 | Aug. 16, 1996 | HB-12169 |
| SEAM-2 | Jul. 30, 1997 | CRL-12380 |
| SEAM-12 | Jul. 30, 1997 | CRL-12381 |

We claim:

1. A method for identifying a molecular mimetic of a unique epitope of *Neisseria meningitidis* serogroup B (MenB), said method comprising:
   (a) providing a library of molecules comprising a putative molecular mimetic of a unique epitope of MenB, wherein said library of molecules is selected from the group consisting of a peptoid library, a peptide library and a phage-display library;
   (b) contacting said library of molecules with an isolated antibody immunologically reactive with an N-acyl-substituted *Neisseria meningitidis* serogroup B capsular polysaccharide, wherein said antibody is not autoreactive with *Neisseria meningitidis* serogroup B capsular polysaccharide as determined by measuring the ability of said antibody to react with human neuroblastoma cell line CHP-134, under conditions that allow immunological binding between said antibody and said molecular mimetic, if present, to provide a complex; and
   (c) separating the complex from non-bound molecules; and
   (d) identifying the molecular mimetic present in the complex.

2. The method of claim 1 wherein said library of molecules is a peptoid library.

3. The method of claim 1 wherein said library of molecules is a peptide library.

4. The method of claim 1 wherein said library of molecules is phage-display library.

* * * * *

SEQUENCE LISTING

<160> NUMBER OF SEQ ID NOS: 68

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 1

Pro Leu Arg Ser Leu Arg Ser Tyr Trp
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 2

Ser Asn Cys Glu Ile Trp Arg Val Gly Cys
 1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 3

Cys Met Arg Tyr Glu Ala Thr Cys
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 4

Cys Gly Leu Pro Arg Phe Arg Cys
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 5

Tyr Cys Gln Ile Gln Gly Ser Cys
 1               5

<210> SEQ ID NO 6
<211> LENGTH: 10
<212> TYPE: PRT
<213> ORGANISM: Artificial Sequence

```
<220> FEATURE:
<223> OTHER INFORMATION: Description of Artificial Sequence: sequence
      from a phage display peptide library

<400> SEQUENCE: 6

Gln Val Pro Cys Ser Ser Arg Arg Gly Cys
  1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 7

Arg Tyr Gly Cys Leu Leu Met Arg Gly Cys
  1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 8

Phe His Cys Lys Val Asn Arg Gly Cys
  1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 9

Ser Cys Arg Ser Lys Asn Ser Ala Gly Cys
  1               5                  10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 10

Thr Val Glu Thr Val Glu Ser Cys
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 11

Tyr Gln Gly Pro Leu Gly Trp Arg
  1               5
```

```
<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 12

Cys Trp Pro Thr Leu Glu Gly Cys
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 13

Cys Leu Thr Ser Trp Ser Ser Cys
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 14

Cys Gly Leu Glu Leu Gln Gly Cys
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 15

Cys Thr Thr Ile Met Cys Ser Thr
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 16

Gly Tyr Glu Val Gln Pro Phe His
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library
```

```
<400> SEQUENCE: 17

Val Ala Lys Thr Val Arg Pro Pro
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 18

Trp Ala Ser Trp Val Gly Gly Pro
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 19

Asp Asp Gly Tyr Glu Ile Arg Trp
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 20

Ser Arg Met Gly Gly Arg Arg
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 21

His Asn Lys Ser Lys Leu Glu Ala
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 22

Gly His Gly Ala Tyr Thr Arg Leu
 1               5

<210> SEQ ID NO 23
<211> LENGTH: 8
<212> TYPE: PRT
```

```
<213> ORGANISM: Artificial Sequence
<220> FEATURE:
<223> OTHER INFORMATION: Description of Artificial Sequence: sequence
      from a phage display peptide library

<400> SEQUENCE: 23

Lys Ser Leu Asn Ala Met Val Leu
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 24

Pro Trp Ser Arg Leu Lys Ser Pro
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 25

Pro Ser Lys Gly Lys Val Leu Ser
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 26

Gly Pro Met Ser Ile Asp Leu Arg
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 27

Arg Thr Glu Leu Gly Trp Arg Tyr
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 28

Ser Asp Ser Gly Cys Tyr Gly Tyr
 1               5
```

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 29

Cys Gly Thr Gln His Val Gly Cys
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 30

Cys Gly Thr His Asp Leu Ala Cys
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 31

Cys Gln Lys Gly Ala Arg Gly Cys
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 32

Cys Ser Arg Tyr Asn Gly Gly Cys
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 33

Cys Gly Arg Ser Thr Glu Leu Cys
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

```
<400> SEQUENCE: 34

Cys Arg Asn Ser Gln Gly Tyr Cys
  1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 35

Leu Asp Ser Gln Leu Arg Arg Thr
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 36

Gly Trp Leu Phe Arg Gly Leu Met
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 37

Leu Asn Phe Lys Val Arg His Asn
  1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 38

Ala Lys Ser Val His Tyr Gly Ile
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 39

Cys Val Ala Leu Met Gly Gly Cys
  1               5

<210> SEQ ID NO 40
<211> LENGTH: 10
```

```
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 40

Cys Gln Lys Gly Ala Arg Ala Arg Gly Cys
 1               5                  10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 41

Phe Ala Ala Ala Leu Gly Gln Asn
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 42

Tyr Ser His Trp Lys Trp Arg Trp
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 43

Gln Met Arg Pro Ala Leu Asn Ser
 1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 44

Trp Leu Asp Arg Gly Ser Thr Pro
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 45

Asp Trp Asp Arg Ala Val Val Leu
```

-continued

```
<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 46

Phe Pro Leu Leu Arg Gly Ala Arg
 1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 47

Phe Ala Trp Ser Cys Thr Trp Pro Gly Cys
 1               5                  10

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 48

Lys Leu His Val Gly Pro Arg Asn
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 49

Leu Phe Pro Lys Pro Arg Leu Pro
 1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 50

Tyr Leu Gly Thr Ser Arg Asn Gly Leu
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: sequence
```

```
        from a phage display peptide library

<400> SEQUENCE: 51

Cys Gly Thr His Asp Leu Ala Cys
 1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 52

Cys Gly Ser Ala Phe Ser Ala His Pro
 1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 53

Ser Trp Trp His Asn Tyr Cys Pro Gly Cys
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 54

Glu Arg Cys Ala Cys Gly Arg Gly Gly Cys
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 55

Glu Thr Lys Glu Arg Gly Glu Ser Gly Cys
 1               5                  10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 56

Ala Phe Cys Cys Gly Ser Gly Thr Arg Gly Cys
 1               5                  10

<210> SEQ ID NO 57
```

<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 57

Ala Phe Cys Gly Ser Gly Thr Arg Gly Cys
 1               5                  10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 58

Asn Leu Ser Ser Pro Cys Gly Arg Gly Cys
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 59

Val Ala Cys Arg Ser Gly Met Gly Gly Cys
 1               5                  10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 60

Ile Arg Ser Gly Cys Arg Pro Val Gly Cys
 1               5                  10

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 61

Cys Trp Lys Pro Gly Arg Ser Gly Cys
 1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 62

```
Phe Val Arg Gly Val Gly Val Gly Cys
 1               5
```

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 63

```
Gly Cys Trp Arg Trp Ile Gln Pro Gly Cys
 1               5                  10
```

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 64

```
Phe Ala Trp Ser Cys Thr Trp Pro Gly Cys
 1               5                  10
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 65

```
Arg Cys Arg Gly His Gly Gly Pro Gly Cys
 1               5                  10
```

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 66

```
Phe Ala Trp Ser Cys Thr Trp Pro Gly Cys
 1               5                  10
```

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: sequence
      from a phage display peptide library

<400> SEQUENCE: 67

```
Cys Asn Leu Arg Met Ser Ser Ala Gly Cys
 1               5                  10
```

<210> SEQ ID NO 68
<211> LENGTH: 6
<212> TYPE: PRT
<213> ORGANISM: Artificial Sequence
<220> FEATURE:

```
-continued

<223> OTHER INFORMATION: Description of Artificial Sequence: soluble
      irrelevant peptide

<400> SEQUENCE: 68

Gln Trp Glu Arg Thr Tyr
 1               5
```